(12) United States Patent
Ramakrishnan et al.

(10) Patent No.: US 7,606,670 B2
(45) Date of Patent: *Oct. 20, 2009

(54) CRYSTAL STRUCTURE OF THE 30S RIBOSOME AND ITS USE

(75) Inventors: Venkatraman Ramakrishnan, Cambridge (GB); Brian Thomas Wimberly, Guilford, CT (US); Ditlev Egeskov Brodersen, Cambridge (GB); Andrew Philip Carter, Cambridge (GB); William Melvon Clemons, Jr., Boston, MA (US)

(73) Assignees: University of Utah Research Foundation, Salt Lake City, UT (US); Medical Research Council, London (GB)

(*) Notice: Subject to any disclaimer, the term of this patent is extended or adjusted under 35 U.S.C. 154(b) by 337 days.

This patent is subject to a terminal disclaimer.

(21) Appl. No.: 09/953,807

(22) Filed: Sep. 17, 2001

(65) Prior Publication Data

US 2005/0154538 A1    Jul. 14, 2005

Related U.S. Application Data

(63) Continuation-in-part of application No. 09/904,779, filed on Jul. 13, 2001, now Pat. No. 6,925,394.

(30) Foreign Application Priority Data

Jul. 14, 2000 (GB) ................... 0017376.5
Sep. 19, 2000 (GB) ................... 0022943.5

(51) Int. Cl.
*G06F 19/00* (2006.01)
*C12Q 1/00* (2006.01)
*G01N 33/48* (2006.01)
*G01N 31/00* (2006.01)
*G06G 7/48* (2006.01)

(52) U.S. Cl. .............. 702/27; 435/4; 702/19; 702/22; 703/11

(58) Field of Classification Search ............. 702/27; 530/350
See application file for complete search history.

(56) References Cited

OTHER PUBLICATIONS

Jan Drenth, Principles of Protein X-ray Crystallography, 1995, Springer-Verlag, p. 16.*
News Focus, Science, Nov. 1, 2002, vol. 298, pp. 948-950.*
Hermann et al., J. Med. Chem., vol. 42, pp. 1250-1261, 1999.*
Purohit et al., Nature, vol. 370, pp. 659-662, 1994.*
Lorber et al., Protein Science, vol. 7, pp. 938-950, 1998.*

(Continued)

*Primary Examiner*—Carolyn L. Smith
(74) *Attorney, Agent, or Firm*—Ivor R. Elrifi; Heidi A. Erlacher; Mintz, Levin, Cohn, Ferris, Glovsky and Popeo, P.C.

(57) ABSTRACT

The invention provides an X-ray crystal structure of the 30S ribosome, obtained from *Thermus thermophilus* 30S subunit, having a tetragonal space group $P4_12_12$ with unit cell dimensions of a=401.4±4.0 Å, b=401.4±4.0 Å, c=175.9±5.0 Å. An advantageous feature of the structure is that it diffracts beyond 3 Å resolution. The invention also provides a crystal of 30S having the three dimensional atomic coordinates of the 30S ribosome, the coordinates being provided in Tables 1A and 1B. The data may be used for the rational design and modelling of inhibitors for the 30S ribosome, which have potential use as antibiotics.

4 Claims, 1 Drawing Sheet

OTHER PUBLICATIONS

Voet et al., Biochemistry, John Wiley & Sons, Inc., p. 931, 1990.*

Bhuyan, et al. (1961). "Pactamycin, A New Antitumor Antibiotic: Discover and Biological Properties," *Antimicrob Agents Chemother* 184-190.

Böck, et al. (1979). "Ribosomal Ambiguity (Ram) Mutations Facilitate Dihydrostreptomycin Binding to Ribosomes," *FEBS Letters* 104(2):317-321.

Brink, et al. (1994). "Spectinomycin Interacts Specifically with the Residues G1064 and C1192 in 16S rRNA, Thereby Potentially Freezing This Molecule Into an Inactive Conformation," *Nucleic Acids Res* 22(3):325-331.

Brodersen, et al. "The Structural Basis for the Action of the Antibiotics Tetracycline, Pactamycin and Hygromycin B on the 30S Ribosomal Subunit," *Cell* 103:1143-1154, 2000.

Brown, et al. (1993). Two Regions of the *Escherichia coli* 16S Ribosomal RNA Are Important for Decoding Stop Signals in Polypeptide Chain Termination, *Nucleic Acids Res* 21(9):2109-2115.

Cabanas, et al. (1978). "Inhibition of Ribosomal Translocation by Aminoglycoside Antibiotics," *Biochem Biophys Res Commun* 83(3):991-997.

Carter, et al. (2000). "Functional Insights from the Structure of the 30S Ribosomal Subunit and its Interactions with Antibiotics," *Nature* 407:340-348.

Chopra, et al. (1992). "Tectracyclines, Molecular and Clinical Aspects," *J. Antimicrob Chemother* 29:245-277.

Clemons, et al. (1999). "Structure of a Bacterial 30S Ribosomal Subunit at 5.5 Å Resolution," *Nature* 400:833-840.

Clemons, et al. (2001). "Crystal Structure of the 30S Ribosomal Subunit from *Thermus thermophilus*: Purification, Crystallization and Structure Determination," *J. Mol. Biol.* 310:827-843.

Cohen, et al. (1969). "Inhibition by Pactamycin of the Initiation of Protein Synthesis. Effect on the 30S Ribosomal Subunit," *Biochemistry* 8(4):1327-1335.

De la Fortelle and Bricogne (1997). "Maximum-Likelihood Heavy-Atom Parameter Refinement for Multiple Isomorphous Replacement and Multiwavelength Anomalous Diffraction Methods," In *Methods in Enzymology*, eds. Carter, C.W., Jr. Sweet, R.M., Academic Press, New York, 1997, pp. 472-493.

Donner and Kurland (1972). "Changes in the Primary Structure of a Mutationally Altered Ribosomal Protein S4 of *Escherichia coli*," *Mol Gen Genet* 115:49-53.

Egebjerg and Garrett. (1991). "Binding Sites of the Antibiotics Pactamycin and Celesticetin on Ribosomal RNAs," *Biochimie* 73:1145-1149.

Eustice and Wilhelm (1984). "Mechanisms of Action of Aminoglycoside Antibiotics in Eucaryotic Protein Syntheses," *Antimicrob Agents Chemother* 26(1):53-60.

Eustice and Wilhelm (1984). "Fidelity of the Eukaryotic Codon-Anticodon Interaction: Interference by Aminoglycoside Antibiotics," *Biochemistry* 23:1462-1467.

Fourmy, et al. (1996). "Structure of the A Site of *Escherichia coli* 16S Ribosomal RNA Complexed with an Aminoglycoside Antibiotic," *Science* 274:1367-1371.

Funatsu and Wittmann (1972). "Location of Amino-Acid Replacements in Protein S12 Isolated from *Escherichia coli* Mutants Resistant to Streptomycin," *J. Mol Biol* 68:547-550.

Funatsu, et al (1972). "Ribosomal Proteins. XXXI. Comparative Studies on Altered Proteins S4 of Sic *Escherichia coli* Revertants from Streptomycin Dependence," *Mol Gen Genet* 115:131-139.

Geigenmüller and Nierhaus (1986). "Tetracycline Can Inhibit tRNA Binding to the Ribosomal P Site as Well as to the A Site," *Eur J. Biochem* 161:723-726.

Gonzales, et al. (1978). "Studies on The Mode of Action of Hygromycin B, An Inhibitor of Translocation in Eukaryotes," *Biochim Biophys Acta* 521:459-469.

Gravel, et al. (1987). "Cross-Linking of Streptomycin to the 16S Ribosomal RNA of *Escherichia coli*," *Biochemistry* 26:6227-6232.

Hope, et al (1989). "Cryocrystallography of Ribosomal Particles," *Acta Cryst.* B45:190-199.

Ito and Wittmann (1973). "Amino Acid Replacements in Proteins S5 and S12 of Two *Escherichia coli* Revertants from Streptomycin Dependence to Independence," *Mol. Gen. Genet* 127:19-32.

Kolesnikov, et al. (1996). "Tetrycyclines Induce Changes in Accessibility of Ribosomal Proteins to Proteases," *Biochimie* 78:868-873.

Kurland, et al (1996.). "Limitations of Translational Accuracy" Chapter 65 in *Escherichia coli and Salmonella, Cellular and Molecular Biology*, Second Edition, vol. 2, Neidhart, F.C. et all, eds. American Society for Microbiology Press, Washington D.C., pp. 979-1004. Includes Table of Contents.

Leclerc, et al. (1991). "Mutations in the 915 Region of *Escherichia coli* 16S Ribosomal RNA Reduce the Binding of Streptomycin to the Ribosome," *Nucleic Acids Res.* 19(14):3973:3977.

Manavathu, et al. (1990). "Molecular Studies on the Mechanism of Tetracycline Resistance Mediated by Tet(O)," *Antimicrob Agents Chemother* 34(1):71-77.

Mann and Bromer (1958). "The Isolation of a Second Antibiotic from Streptomyces Hygroscopicus," *J. Am. Chem. Soc.* 80:2714-2716.

Melançon, et al. (1984). "Cross Lining of Streptomycin to the 30S Subunit of *Escherichia coli* with Phenyldiglyoxal," *Biochemistry* 23:6697-6703.

Melançon, et al. (1988). "A Mutation in the 530 Loop of *Escherichia coli* 16S Ribosomal RNA Causes Resistance to Streptomycin," *Nucleic Acids Res* 16(2):9631-9339.

Moazed and Noller (1987). "Interaction of Antibiotics with Functional Sites in 16S Ribosomal RNA," *Nature* 337:389-394.

Montadon, et al. (1985). "Streptomycin-Resistance of *Euglena gracilis* Chloroplasts: Identification of a Pint Mutation in the 16S rRNA Gene in an Invariant Position," *Nucleic Acids Res.* 13(12):4299-4310.

Montandon, et al. (1986). "*E. coli* Ribosomes with a C912 to U Base Change in the 16s rRNA are Streptomycin Resistant," *EMBO J.* 5(3):3705-3708.

Mueller and Brimacombe (1997). "A New Model for the Three-Dimensional Folding of *Escherichia coli* 16S Ribosomal RNA. I. Fitting the RNA to a 3D Electron Microscopic Map at 20 Å," *J. Mol. Biol.* 271:524-544.

Oehler, et al. (1997). "Interaction of Tatracycline with RNA: Photoincorporation into Ribosomal RNA of *Escherichia coli*," *Nucleic Acid Res* 25(6):1219-1224.

Ogle, et al. (2001). "Recognition of Cognate Transfer RNA by the 30S Ribosomal Subunit," *Science* 292:897-902.

Pape, et al. (2000). "Conformational Switch in the Decoding Region of 16s rRNA During Aminoacyl-tRNA Selection n the Ribosome," *Nat. Struct. Biol.* 7(2):104-107.

Pinard, et al. (1993). "The 5' Proximal Helix of 16S rRNA is Involved in the Binding of Streptomycin to the Ribosome," *FASEB* J. 7:173:176.

Pioletti, et al. (2001). "Crystal Structures of Complexes of the Small Ribosomal Subunit with Tetracycline, Edeine and IF3," *EMBO Journal* 20(8):1829-1839.

Powers and Noller (1991). "A Functional Pseudoknot in 16S Ribosomal RNA," *Embo J.* 10:2203-2214.

Ross, et al. (1998). "16S rRNA Mutation Associated with Tetracycline Resistance in a Gram-Positive Bacterium," *Antimicrob Agent Chemother* 42(7):1702-1705.

Schluenzen, et al. (2000). "Structure of Functionally Activated Small Ribosomal Subunit at 3.3 Å Resolution," *Cell* 102:615-623.

Spahn and Prescott (1996). "Throwing a Spanner in the Works: Antibiotics and the Translation Apparatus," *J. Mol Med* 74:423-439.

Spangler and Blackburn (1985). "The Nucleotide Sequence of the 17S Ribosomal RNA Gene of Tetrahymena Thermophila and the Identification of Point Mutations Resulting in Resistance to the Antibiotics Paramomycin and Hygromycin," *J. Biol. Chem.* 260(10):6334-6340.

Trejedor, et al. (1985). "Photoaffinity Labeling of the Pactamycin Binding Site on Eubacterial Ribosomes," *Biochemistry* 24:3667-3672.

Timms, et al. (1992). "Mutant Sequences in the rpsL Gene of *Eschrichia coli* B/r: Mechanistic Implications for Spontaneous and Ultraviolet Light Mutagenesis," *Mol Gen Genet* 232:89-96.

Timms and Bridges (1993). "Double, Independent Mutational Events in the rpsLGene of *Escherichia coli* and Example of Hypermutability," *Mol. Microbiol.* 9(2):335-342.

Tubulekas, et al. (1991). "Mutant Ribosomes Can Generate Dominant Kirromycin Resistance," *J. Bacteriol.* 173(12):3635-3643.

Van Loock, et al. "Major Groove Binding of the tRNA/mRNA Complex to the 16S Ribosomal RNA Decoding Site," *J. Mol. Biol.* 285:2069-2078, 1999.

Woodcock, et al. (1991). "Interaction of Antibiotics with A- and P-Site-Specific Bases in 16S Ribosomal RNA," *EMBO J.* 10:3099-3103.

Yoshizawa, et al. (1999). "Recognition of the Codon-Anticodon Helix by Ribosomal RNA," *Science* 285:1722-1725.

Zierhut, et al. (1979). "Comparative Analysis of the Effect of Aminogycosides on Bacterial Protein Synthesis In Vitro," *Eur. J. Biochem.* 98:577-583.

Otwinowski and Minor (1997). "Processing of X-Ray Diffraction Data Collected in Oscillation Mode," *Methods in Enzymology* 276:307-326.

Aboul-ela, et al., "Structure of HIV-1 TAR RNA in the absence of ligands reveals a novel conformation of the trinucleotide bulge," *Nucleic Acids Research*, 24(20):3974-3981, 1996.

Fourmy, et al., "Paromomycin binding induces a local conformational change in the A-site of 16 S rRNA," *J. Mol. Biol.*, 277:333-345, 1998.

Jiang, et al., "Saccharide-RNA recognition in an aminoglycoside antibiotic-RNA aptamer complex," Chemistry and Biology, 4:35-50, Jan. 1997.

Jiang, et al., "Solution structure of the tobramycin-RNA aptamer complex," *Nature Structural Biology*, 5(9):769-774, Sep. 1998.

\* cited by examiner

SEQUENCE LISTING

```
<160> NUMBER OF SEQ ID NOS: 1

<210> SEQ ID NO 1
<211> LENGTH: 20
<212> TYPE: PRT
<213> ORGANISM: artificial
<220> FEATURE:
<223> OTHER INFORMATION: zinc finger motif
<220> FEATURE:
<221> NAME/KEY: misc_feature
<222> LOCATION: (2)..(3)
<223> OTHER INFORMATION: X can be any amino acid
<220> FEATURE:
<221> NAME/KEY: misc_feature
<222> LOCATION: (5)..(16)
<223> OTHER INFORMATION: X can be any amino acid
<220> FEATURE:
<221> NAME/KEY: misc_feature
<222> LOCATION: (18)..(19)
<223> OTHER INFORMATION: X can be any amino acid

<400> SEQUENCE: 1

Cys Xaa Xaa Cys Xaa Xaa Xaa Xaa Xaa Xaa Xaa Xaa Xaa Xaa Xaa Xaa
1               5                   10                  15

Cys Xaa Xaa Cys
            20
```

CRYSTAL STRUCTURE OF THE 30S RIBOSOME AND ITS USE

CROSS REFERENCE TO RELATED APPLICATIONS

This application claims priority from United Kingdom (U.K.) applications 0017376.5 filed Jul. 14, 2000 and 0022943.5 filed Sep. 19, 2000, the contents of which are incorporated herein by reference. This application is a continuation in part application of U.S. Ser. No. 09/904,779.

This invention was made in part with U.S. Government support under NIH grant GM 44973 awarded by the PHS. The U.S. Government has certain rights in the invention.

FIELD OF THE INVENTION

The present invention relates to the provision of a high resolution crystal structure of the prokaryotic 30S ribosome subunit, and the use of this structure in drug discovery.

BACKGROUND OF THE INVENTION

The wealth of information made available through efforts in structural genomics and advances in computation has allowed structure-based drug design to emerge as a valuable tool in medicinal chemistry. In the past combinatorial chemistry, coupled with high-throughput approaches, shifted attention away from the more structure-based methods. Large-scale determination of protein structures is reversing the drug discovery process by starting with the protein structure and using it to identify and design new ligands. It is the integration of structure-based methods, virtual screening, and combinatorial chemistry that will provide the basis for more efficient drug design in the future, significantly reducing the time of the design cycle and the cost per marketed drug. Significant advances have already been made in AIDS, arthritis and cancer and in the treatment of hypertension (e.g. captopril).

Translation of the genetic code occurs on the ribosome, a large nucleoprotein complex that consists of two subunits. In bacteria, the two subunits are denoted 30S and 50S. The 50S subunit contains the catalytic site of peptidyl transferase activity, while the 30S subunit plays a crucial role in decoding messenger RNA. Protein synthesis is a complex, multistep process that requires several extrinsic GTP-hydrolysing protein factors during each of the main stages of initiation, elongation and termination. Despite several decades of work, the molecular details of the process are poorly understood, and the elucidation of the mechanism of translation is one of the fundamental problems in molecular biology today. A recent collection of articles summarizes the state of understanding of the field [1].

A contribution to this problem was made by Yonath and co-workers, who after nearly a decade of work showed that structures as large as the 50S ribosomal subunit would form crystals that diffract beyond 3 Å resolution [2]. The 30S ribosomal subunit (hereafter referred to as 30S) from *Thermus thermophilus* was originally crystallized by Trakhanov et al. in 2-methyl-2,4-pentanediol (MPD) [3] and soon afterwards by Yonath and co-workers in a mixture of ethyl-butanol and ethanol [4]. Subsequent work by both groups showed that the MPD crystal form diffracted to about 9-12 Å resolution [5, 6]. The diffraction limit of these crystals did not improve beyond 7 Å resolution for almost a decade, but more recently both Yonath and co-workers [7, 8] and Clemens et al. [9] obtained crystals of the MPD form that exhibit significantly improved diffraction. However, unlike the crystals obtained by the Yonath group [6], crystals, prepared according to the invention, do not require soaking in tungsten clusters or heat treatment in order to obtain high-resolution diffraction.

The structure of the 30S at 5.5 Å resolution [9] has been described previously. All seven proteins whose structures were known at the time were placed in an electron density map. The structure of protein S20 was inferred to be a three-helix bundle, the fold of an entire domain of 16S RNA was traced, and a long RNA helix at the interface that contains the decoding site of the 30S was identified. Proteins S5 and S7 were also placed in electron density maps of the 30S obtained by Yonath and co-workers.

The 30S ribosomal subunit is a major target for antibiotics. The ribosome is a useful target for antibiotics since the structure of the 30S is widely conserved between prokaryotes, allowing for broad spectrum antibiotics. However, resistance to current antibiotics is currently a major problem in the field of medicine. There are presently very few new antibiotics available which can be used to treat the highly resistant strains of bacteria such as MRSA (methicilin resistant *Staphylococcus aureus*) which are becoming increasingly widespread.

Antibiotics act by interfering with various aspects of ribosome function. A detailed knowledge of antibiotic interactions with the ribosome could aid the development of new drugs against increasingly resistant strains of bacteria. 30S crystal structures described in the prior art are of relatively low resolution (greater than 3 Å). There is thus a need for a high-resolution structure, which can be useful in the development of novel therapeutics.

All references cited herein, including published patent applications and publications, are incorporated by reference in their entirety.

SUMMARY OF THE INVENTION

The invention is based upon determination of the structure of the 30S ribosomal subunit at 3 Å resolution. The structure contains all of the ordered regions of 16S RNA and 20 associated proteins, and contains over 99% of the RNA sequence and 95% of the protein sequences, with the missing parts being exclusively at the termini of RNA or polypeptide chains. The invention provides a description of the overall architecture and the main structural features of the 30S subunit.

The refined atomic resolution model of the 30S presented here allows the interpretation of a vast amount of biochemical data on its function in precise structural terms. The structure will also serve as a basis for the interpretation in molecular terms of lower resolution models of various functional states by electron microscopy or X-ray crystallography. The 30S structure will help produce testable models for various aspects of ribosome function.

The invention provides for a crystal of a 30S subunit having a tetragonal space group $P4_12_12$ with unit cell dimensions of a=401.375 Å, b=401.375 Å, c=175.887 Å.

The invention also provides for a crystal of a 30S subunit having a tetragonal space group $P4_12_12$ with unit cell dimensions of a=401.4 Å, b=401.4 Å, c=175.9 Å.

The invention also provides for a crystal of a 30S ribosomal subunit having a resolution less than 3 Å.

In another aspect, the invention also provides a crystal of 30S having the three dimensional atomic coordinates of the 30S ribosome.

The invention also provides for a crystal of a 30S ribosomal subunit having the structure defined by the co-ordinates of Table 1.

Table 1A provides a set of atomic coordinates of the 30S ribosome. Table 1B provides a set based upon the coordinates of Table 1A but which have been refined further from the data. Reference herein to "Table 1" is a reference to either of Table 1A or 1B (or where the context permits, both; i.e., reference to "Table 1" refers to Table 1A and/or Table 1B). Thus, for example, where it is stated that the invention refers to computer readable media with "atomic coordinate data according to Table 1 recorded thereon", this means that the media has either the data of Table 1A, or the data of Table 1B, or both, recorded thereon.

In one embodiment, the structure is formed by a method that does not use heavy atom clusters or heat activation.

In another embodiment the 16S RNA of the crystal structure of the 30S subunit comprises the 885-888/910-912 base pairing conformation.

In another embodiment, the 30S subunit crystals do not comprise the S1 subunit protein.

The invention also provides for a computer-based method of rational drug design which comprises: (a) providing the structure of a 30S ribosomal subunit as defined by the coordinates of Table 1; (b) providing the structure of a candidate modulator molecule; (c) fitting the structure of the candidate to the structure of the 30S of Table 1; and d) comparing the result with a structure comprising the 30S ribosome of Table 1.

The invention also provides for a computer-based method of rational drug design comprising the steps of: (a) providing the structure of the 16S RNA of the 30S ribosome as defined by the coordinates of Table 1, (b) providing the structure of a candidate modulator molecule, (c) fitting the structure of the candidate to the structure of the 16S RNA of the 30S ribosome to provide a result; and (d) comparing the result with a structure comprising the 16S RNA of the 30S ribosome of Table 1.

The invention also provides for a computer-based method of rational drug design comprising the steps of: (a) providing the coordinates of at least one atom of the 30S ribosome as presented in Table 1, (b) providing the structure of a candidate modulator molecule, (c) fitting the structure of the candidate to the coordinates of the 30S ribosome to provide a result; and (d) comparing the result with a structure comprising the coordinates of the 30S ribosome of Table 1.

The invention also provides for a computer-based method of rational drug design comprising the steps of: (a) providing the coordinates of at least a sub-domain of the 30S ribosome, (b) providing the structure of a candidate modulator molecule, (c) fitting the structure of the candidate to the coordinates of the 30S ribosome to provide a result; and (d) comparing the result with a structure comprising the coordinates of the 30S ribosome sub-domain of Table 1.

The invention also provides for a computer-based method for identifying a potential inhibitor of the 30S ribosome comprising the steps of: (a) employing a three-dimensional structure of 30S, or at least one sub-domain thereof, to characterise at least one active site, the three-dimensional structure being defined by atomic coordinate data according to Table 1; and (b) identifying the potential inhibitor by designing or selecting a compound for interaction with the active site.

In one embodiment, this computer-based method for identifying a potential inhibitor of the 30S ribosome further comprises the steps of: (c) obtaining or synthesising the potential inhibitor; (d) contacting the potential inhibitor with 30S to determine the ability of the inhibitor to interact with the 30S.

In another embodiment, this computer-based method for identifying a potential inhibitor of the 30S ribosome further comprises the steps of: (c) obtaining or synthesising the potential ligand; (d) forming a complex of 30S and the potential ligand; and (e) analysing the complex by X-ray crystallography to determine the ability of the potential ligand to interact with 30S.

30S crystals do not contain the S1 subunit protein. Selective removal of the S1 subunit prior to crystallization is shown to improve the resolution of the crystals of the 30S subunit according to the invention described herein. Although the atomic co-ordinates, provided in Table 1 below, allow those of skill in the art to bypass the need to undertake the crystallization of the 30S, this crystallization method nonetheless forms a further aspect of the invention.

The invention also provides for a method for the determination of the structure of a bacterial ribosomal 30S subunit which method comprises: (a) crystallising the 30S of the species to obtain a crystal; (b) performing X-ray crystallography on the crystal to obtain X-ray diffraction data; (c) providing the structure data of Table 1; and (d) using molecular replacement to calculate an electron density map of the 30S.

In one embodiment of this method, the S1 subunit is removed from the 30S prior to the crystallization step.

In another embodiment of this method, the crystallization is performed under conditions wherein crystals only form from a 30S subunit that lacks the S1 subunit.

The invention also provides for a computer system, for generating structures and/or performing rational drug design for the 30S ribosome or complexes of the 30S ribosome with a potential modulator, the system comprising either (a) atomic coordinate data according to Table 1, the data defining the three-dimensional structure of 30S or at least one sub-domain thereof, or (b) structure factor data for 30S, the structure factor data being derivable from the atomic coordinate data of Table 1.

The invention also provides for a computer readable media with either (a) atomic coordinate data according to Table 1 recorded thereon, the data defining the three-dimensional structure of the 30S ribosome, or at least one atom or at least one sub-domain thereof, or (b) structure factor data for the 30S ribosome recorded thereon, the structure factor data being derivable from the atomic coordinate data of Table 1.

The invention also provides for a method for modelling a structure of a 30S ribosome comprising the steps of: a) providing an atomic model of a structure wherein the structure has a resolution of greater than 3 Å, b) comparing the structure obtained in a) with the data presented in Table 1, and c) refining the model to resolve the structure and provide higher resolution.

In one embodiment of this method, the 30S ribosome is from a bacterial source that is not *T. thermophilis*.

The invention also provides for a method for crystallizing a 30S subunit comprising the steps of: a) providing a 30S subunit, b) removing the S1 subunit therefrom, c) crystallizing the 30S subunit; and d) freezing the crystal.

The invention also provides for a method for crystallizing a 30S subunit comprising the steps of: a) providing a 30S subunit, b) crystallizing the 30S subunit; and c) freezing the crystal, wherein the crystallization is performed under conditions wherein crystals only form from a 30S subunit that lacks the S1 subunit.

The invention also provides for a method of identifying a binding partner of a 30S subunit comprising the steps of: a) characterizing an active site of the 30S subunit, and b) designing or selecting a compound that interacts with the active site.

In one embodiment of this method, the active site is characterized from the three-dimensional structure of the 30S subunit.

In another embodiment of this method, the active site is characterized from the three-dimensional structure of at least one sub-domain of the 30S subunit.

In another embodiment of this method, the binding partner is an inhibitor of the 30S subunit.

The invention also provides a method of designing a molecule that interacts with the 30S subunit, comprising analyzing the three dimensional structure of the 30S subunit by a computer modelling program.

The invention also provides a method of preparing a computer fitting model of binding of a binding partner of the 30S subunit and the 30S subunit comprising analyzing the binding partner and the 30S subunit by a docking program selected from the group consisting of: GRAM, DOCK, AUTODOCK or GRID.

The invention also provides a method of determining the activity of a binding partner of the 30S subunit comprising the steps of: a) obtaining or synthesizing the binding partner, and b) contacting the 30S subunit with the binding partner under conditions wherein the binding partner is active; and c) determining the activity of the 30S subunit.

The invention also provides a method of characterizing the binding of a binding partner of the 30S subunit to the 30S subunit comprising the steps of: a) obtaining or synthesizing the binding partner, b) contacting the 30S subunit with the binding partner, c) forming a complex of the 30S subunit and the binding partner, and d) analyzing the complex by X-ray crystallography.

In one embodiment, the binding partner is an inhibitor of the 30S subunit.

The invention also provides a method of analyzing a 30S-ligand complex comprising the steps of: a) obtaining X-ray crystallographic diffraction data from the 30S-ligand complex, b) obtaining a three-dimensional structure of the 30S subunit or at least one subdomain of the 30S subunit, and c) using the data obtained in a) and b) to generate a difference Fourier electron density map of the complex.

In one embodiment of this method, the three-dimensional structure is defined by atomic coordinate data presented in the group consisting of: Table 1, 2, or 3.

In another embodiment of this method, the three dimensional structure is further defined by atomic coordinate data presented in Table 4 or 5.

The invention also provides a method of modelling the structure of a mutant 30S subunit comprising the steps of: a) providing the structure of the 30S ribosome of Table 1, 2 or 3, b) changing at least one amino acid of the structure to provide the mutant 30S subunit, and c) modelling the structure of the 30S mutant.

The invention also provides a method of modelling the structure of a mutant 30S subunit comprising the steps of: a) providing the structure of the 30S ribosome of Table 1, 2 or 3, b) changing at least nucleotide of the structure to provide the mutant 30S subunit, and c) modelling the structure of the 30S mutant.

In one embodiment of this method of modelling, step b) is repeated.

The invention also provides for a method of analyzing a 30S-ligand complex comprising the steps of: a) cocrystallizing the 30S and the ligand or soaking the ligand into crystals of the 30S; b) collecting x-ray crystallographic data from the crystals of the 30S-ligand complex; c) using the three-dimensional structure of Table 1 or at least one sub-domain thereof, to generate a difference Fourier electron density map of the 30S-ligand; and d) modelling the ligand in the difference Fourier electron density map.

In one embodiment, the S1 subunit is removed from the 30S prior to the cocrystallization step.

In another embodiment, the cocrystallization is performed under conditions wherein crystals only form from a 30S subunit that lacks the S1 subunit.

Figure 1:
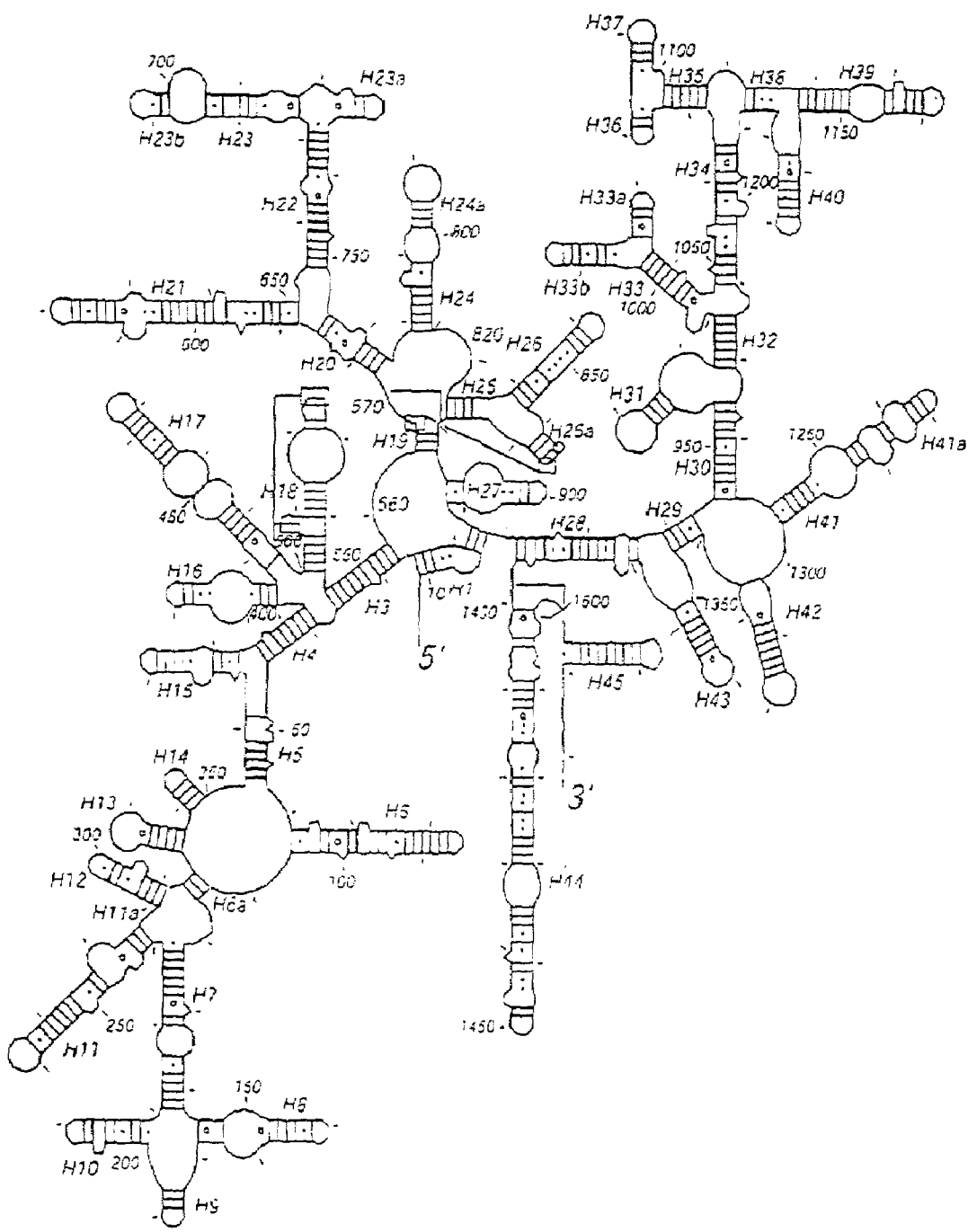
FIG. 1 shows the secondary structure of the 30S ribosome.

DESCRIPTION OF ACCOMPANYING CD-ROM
(37 C.F.R. §§ 1.52 & 1.58).

Tables 1A and 1B referred to herein (also referred herein as Table 1) are filed herewith on CD-ROM in accordance with 37 C.F.R. §§ 1.52 and 1.58. Two identical copies (marked "Copy 1" and "Copy 2") of said CD-ROM, both of which contain Tables 1A and 1B, are submitted herewith, for a total of two CD-ROM discs submitted. Table 1A is recorded on said CD-ROM discs as "Table 1A.txt" created Jul. 12, 2001, size 3,952 KB. Table 1B is recorded on said CD-ROM discs as "Table 1B.txt" created on Jul. 12, 2001, size 4,168 KB.

The contents of the files contained on the CD-ROM discs submitted with this application are hereby incorporated by reference into the specification.

DETAILED DESCRIPTION OF THE INVENTION

The invention provides a high resolution crystal structure of the 30S ribosome subunit and the use of this structure for drug discovery.

Definitions.

"A", "an", "the" and the like, unless otherwise indicated include plural forms.

The term "sub-domain" includes any one or more of the following:

(a) an element selected from the following:
at least one complete element of secondary structure, i.e. an alpha helix or a beta sheet, or RNA helix, as described in the detailed description below;
a group of two or more such elements which interact with each other;
at least one subunit protein;
a subgroup of subunit proteins, for example a group which includes two or more proteins which are found to interact with each other;
any of the above, when the protein(s) or element(s) thereof is used in conjunction with all or part of the 16S RNA structure associated with the element(s) or protein(s);

(b) a space of volume defining a region around any one particular atom of interest (e.g. an atom involved in binding to an antibiotic), the volume being less than the total volume of the tetragonal space of the complete crystal. For example, the coordinates of atoms in a volume of from about 500 to about 15,000 Å$^3$ may be selected and used for the present invention. Such a space may be a sphere having a diameter of from about 10 Å to about 30 Å, centred around a point of interest; and (c) a collection of at least about 10, e.g. at least about 25 such as at least about 50, more preferably at least about 100, even more preferably at least about 500 atoms and most preferably at least about 1000 atoms defined by the coordinates of Table 1, wherein at least 2 of the atoms, and preferably at least about 50% of the atoms of the collection are located within about 50 Å of each other.

An "active site" of the 30S is any part of this structure involved in tRNA or mRNA binding, factor binding or translocation. This includes regions responsible for binding initiation factors, elongation factor G or release factors, regions which are target sites for regulation by co-factors, phosphorylation or acetylation, and regions responsible for interaction with the 50S ribosome. It also includes regions which change conformation during translocation or protein synthesis, particularly one or more of the 16S RNA helixes 18, 27, 34 and 44.

Particular regions of the 30S include antibiotic binding regions. Other regions include the three tRNA binding sites, i.e. the aminoacyl (A), peptidyl (P) and exit (E) sites. Other active sites are those which undergo movement during translocation of tRNAs from the A to P sites and the P to E sites. Regions further include any one of the subunit proteins S2 to S20 and THX, including any of the individually identified subunit proteins in the accompanying examples.

By "fitting", is meant determining by automatic or semi-automatic means, interactions between one or more atoms of a potential inhibitor molecule and one or more atoms or binding sites of the 30S, and calculating the extent to which such interactions are stable. Various computer-based methods for fitting are described further herein.

The term "fit" refers to the result of "fitting" when comparison step shows identical or substantially the same coordinates to a 30S ribosomal subunit bound by one or more antibiotics including but not limited to paromomycin, streptomycin, spectinomycin, tetracycline, pactamycin or hygromycin B as defined herein.

The term "root mean square deviation" means the square root of the arithmetic mean of the squares of the deviations from the mean.

"Computer readable media" refers to any media which can be read and accessed directly by a computer. Such media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

A "computer system" refers to the hardware means, software means and data storage means used to analyse the atomic coordinate data of the present invention. The minimum hardware means of the computer-based systems of the present invention comprises a central processing unit (CPU), input means, output means and data storage means. Desirably a monitor is provided to visualise structure data. The data storage means may be RAM or means for accessing computer readable media of the invention. Examples of such systems are laptops as well as microcomputer workstations available from Silicon Graphics Incorporated and Sun Microsystems running Unix based, Linux, Windows NT or IBM OS/2 operating systems.

A "ligand" is any chemical moiety (organic or inorganic) that binds or interacts, generally but not necessarily specifically, to or with another chemical entity.

The term "space group" refers to the arrangement of symmetry elements of a crystal. The International Union of Crystallographers has determined that there are 230 unique ways in which chemical substances, proteins or otherwise, may assemble in three-dimensions to form crystals. These are called the 230 "space groups." The designation of the space group in addition to the unit cell constants (which define the explicit size and shape of the cell, which repeats within the crystal) is routinely used to uniquely identify a crystalline substance.

A "tetragonal space group" refers to a crystal system characterized by three axes at right angles of which only the two lateral axes are equal.

The term "molecular replacement" refers to a method that involves generating a preliminary atomic model of a crystal, whose structure coordinates are unknown, by orienting and positioning a related crystal structure whose structure coordinates are known. Phases are calculated from this model and combined with the observed amplitudes to give an approximate Fourier synthesis of the structure whose coordinates are unknown. This, in turn, can be subject to any of the several forms of refinement, as defined herein, to provide a final, accurate structure of the unknown crystal. Lattman, E., "Use of the Rotation and Translation Functions," in Methods in Enzymology, 115, pp. 55-77 (1985); M. G. Rossmann, ed., "The Molecular Replacement Method," Int. Sci. Rev. Ser., No. 13, Gordon & Breach, New York, (1972). Using the structure coordinates of a 30S ribosomal subunit provided by this invention, molecular replacement may be used to determine the structure coordinates of a crystalline mutant or homologue of a 30S ribosomal subunit, or of a different crystal form of a 30S ribosomal subunit bound to a modulator compound.

As used herein, the term "modulator" compound refers to a compound that increases or decreases the activity of the 30S ribosomal subunit according to the invention. A candidate modulator may be said to inhibit or decrease activity if the translational activity of the associated intact ribosome is reduced, for example by more than 10%, (for example, 11%, 20%, 30%, 50%, 100% etc) in the presence of a modulator when compared to values obtained in the absence of modulator. A candidate modulator may be said to activate or increase activity if the translational activity of the associated intact ribosome is increased for example by more than 10%, (for example, 11%, 20%, 30%, 50%, 100% etc) in the presence of the modulator when compared to values obtained in the absence of the modulator. A candidate modulator may also be said to activate or increase activity if the translational activity of the associated intact ribosome is increased for example by at least 2-fold, for example 3, 5, 10, 100, 1000 or 10,000-fold or more) in the presence of the modulator when compared to values obtained in the absence of a modulator. A modulator can be a protein, a nucleic acid, or an antibody or fragment thereof, a peptide, an organic molecule etc. . . . Candidate modulators can be natural or synthetic compounds, including, for example, antibiotics and derivatives thereof.

As used herein, the term "forming a complex" refers to covalent or non-covalent association of the 30S subunit of the invention with a candidate modulator compound. A complex may also encompass accessory factors and/or inhibitors or activators associated with the 30S subunit according to the invention.

As used herein, an "interaction" refers to a condition of proximity between a chemical entity or compound, or portions thereof, with the 30S ribosomal subunit according to the invention. The association or interaction may be non-covalent—wherein the juxtaposition is energetically favored by hydrogen bonding or van der Waals or electrostatic interactions—or it may be covalent.

As used herein, "structure coordinates" refers to mathematical coordinates derived from mathematical equations related to the patterns obtained on diffraction of a monochromatic beam of X-rays by the atoms (scattering centers) of a 30S ribosomal subunit complex in crystal form. The diffraction data are used to calculate an electron density map of the repeating unit of the crystal. The electron density maps are then used to establish the positions of the individual atoms within the unit cell of the crystal.

The term "unit cell" refers to a basic parallelepiped shaped block. The entire volume of a crystal may be constructed by regular assembly of such blocks. Each unit cell comprises a complete representation of the unit of pattern, the repetition of which builds up the crystal. Using the structure coordinates of the 30S ribosomal subunit complex provided by this invention, molecular replacement may be used to determine the structure coordinates of a crystalline mutant or homologue of the 30S ribosomal subunit complex or of a different crystal form of the 30S ribosomal subunit bound by a candidate modulator compound such as an antibiotic or other small organic molecule.

In drug design, the binding site for a drug is usually defined by the location of the natural active site or the location of the recognition site for a natural ligand. It is normally found experimentally by studying a complex formed between the target molecule of interest, for example a protein or a 30S ribosomal subunit, and a natural ligand or substrate. "Rational drug design" refers to replacing the natural ligand or substrate by an inert ligand, an inhibitor or some other molecule that alters the natural activity of the 30S ribosomal subunit.

As used herein, the term "determination of the structure" refers to the determination of the three dimensional structure of proteins by X-ray crystallography. Well ordered protein crystals contain multiple arrays of identical molecules that can diffract an X-ray beam giving a defined diffraction pattern from which the structure of the protein molecule can be deduced.

As used herein, the term "contacting" refers to the incubation of an inhibitor compound together with a 30S ribosomal subunit according to the invention under conditions where the inhibitor compound binds to the 30S ribosomal subunit with a dissociation constant as defined herein and in a manner that can be detected by a binding assay of the invention.

As used herein, "three dimensional structure" refers to the spatial arrangement of the 30S subunit polypeptide chains and 16S ribosomal RNA within a protein crystal. The three-dimensional structure of the 30S ribosomal subunit of the invention is defined by a set of structure coordinates as set forth in Table 1. The term "structure coordinates" refers to Cartesian coordinates derived from mathematical equations related to the patterns obtained on diffraction of a monochromatic beam of X-rays by the atoms (scattering centers) of a 30S ribosomal subunit in crystal form. The diffraction data are used to calculate an electron density map of the repeating unit of the crystal. The electron density maps are then used to establish the positions of the individual atoms of the 30S ribosomal subunit or 30S ribosomal subunit bound by a candidate modulator compound. Those of skill in the art will understand that a set of structure coordinates for a 30S ribosomal subunit or a portion thereof, is a relative set of points that define a shape in three dimensions.

As used herein, the term "resolution" refers to the resolution of the electron density map.

The quality of protein crystals is determined by the ability of the crystal to scatter X-rays of wavelengths (typically 1.0 to 1.6 Angstroms) suitable to determine the atomic coordinates of the protein. The measure of the quality is determined as a function of the highest angle of scatter (the ultimate or intrinsic resolution). According to Bragg's Law: $\lambda = 2d \sin \theta$., where $\theta$ represents the reflection angle $\lambda$ the wavelength of the X-ray beam, and d the distance between two adjacent planes that are separated by the length of one of the unit cell axes. d, therefore, represents the resolution of the crystal form in angstroms and is routinely used to judge the ultimate usefulness of protein crystals.

As used herein, the term "higher resolution" refers to a resolution as defined herein of less than 5 Angstrom, preferably less than 3 Angstroms and most preferably equal to or less than 1.5 Angstroms.

As used herein, the term "lower resolution" refers to a resolution as defined herein of greater than 3 Angstroms, preferably greater than 4 Angstroms and most preferably equal to or greater than 5 Angstroms.

As used herein, the term "characterizing the binding" refers to characterizing the association of a modulator compound with the 30S ribosomal subunit that is detectable by a binding assay of the invention. As the term is used herein, binding is "specific" if it occurs with a $K_d$ of 1 mM or less, generally in the range of 500 μM to 10 pM.

As used herein, the term "inhibitor" refers to a compound that binds to the 30S ribosomal subunit with a dissociation constant, as defined herein, and decreases the translational activity of the associated ribosome by at least 10% when compared to the translation activity of the associated ribosome in the absence of inhibitor. According to the invention, "inhibitor" compounds are preferably antibiotics and derivatives thereof.

The term "translational activity" refers to any activity associated with a ribosome, containing the 30S ribosomal subunit, that is required for polypeptide chain synthesis. Translational activity is detected or measured in a translation assay as described herein.

The term "determining the activity" refers to detecting or measuring the translational activity of the ribosome as defined herein. Translational activity can be measured by a number of different assays known to those in the art including but not limited to assays that measure tRNA binding, mRNA binding and amino acid incorporation into a nascent polypeptide chain (as described in Ashraf, S. et al. RNA 5, 503-511; Von Ahsen, U. et al. (1997) RNA 3:49-56 and Zubay G Annu Rev Genet 1973; 7:267-87).

The term "atomic model" refers to the proposed structure of the 30S ribosomal subunit that is deduced by matching the electron density map of the amino acid side chains obtained from X-ray diffraction data to the known sequence of the polypeptide chain.

The term "providing the structure of the 30S ribosomal subunit" refers to providing the three dimensional structure of the 30S ribosomal subunit as deduced from the atomic co-ordinates shown in Table 1.

The term "providing the structure of a candidate modulator molecule" refers to providing the three dimensional structure of a modulator compound as defined in commercially available computer databases, for example Available Chemical Directory (ACD) from the company MDL (US), as well as various electronic catalogues of publicly available compounds such as the National Cancer Institute (NCI, US) catalogue, ComGenex catalogue (Budapest, Hungary), Asinex (Moscow, Russia).

The term "resolving a structure" refers to interpreting an electron density map by superimposing onto it the 30S ribosomal subunit polypeptide chain and 16S RNA of known sequence and stereochemistry. The structure is said to be "resolved" if the electron density map of the 30S ribosomal subunit obtained from the X-ray diffraction data fits or matches the electron density of the polypeptide side chains as predicted from the polypeptide amino acid sequence.

The term "refining a model" refers to the process in which an atomic model is adjusted to minimize the difference between the experimentally observed diffraction amplitudes of a crystal, for example the 30S ribosomal subunit crystal, and those calculated for a hypothetical crystal containing the proposed model.

The term "species other than *thermophilis*" refers to species other than the bacterium *T. thermophilis* including other species of prokaryotes, preferably those species that are pathogenic for humans. These species include gram-positive strains (including but not limited to: *Streptococcus faecalis, Staphylococcus aureus, Streptococcus pneumoniae, Clostridium difficile*), gram-negative strains (including but not limited to: *Escherichia coli, Salmonella typhimurium, Haemophilus influenzae, Neisseria meningitis, Pseudomonas aeruginose, Entesobacter cleacae, Heliobacter pylori, Moraxella catarrhalis, Bacteriodes fragilis*) and others which fall into neither category (including but not limited to *Legionella pneumophila*).

The term "structure factor data" refers to structure factor amplitudes. Structure factor amplitudes represent the normalized amplitudes of the X-ray reflections (spots) that are measured directly in a diffraction experiment.

The term "deriving structure factor data from atomic coodinate data" refers to calculating the structure factors by a simple Fourier transform, using one of a number of standard programs, including SFALL in the CCP4 package or CNS, and the known coordinates, cell dimensions and space group derived from the X ray diffraction data.

The term "designing a compound" refers to using computer programs, known to those in the art (for example Catalyst (Accelrys) and Unity (Tripos)) to identify novel compounds, that are predicted to bind to functionally important regions of the 30S ribosomal subunit and may therefore act as modulators of ribosomal function.

The term "selecting a compound" means identifying and choosing potential modulator compounds from commercially available libraries, for example Available Chemical Directory (ACD) from the company MDL (U.S.) and online catalogues of publicly available compounds such as the National Cancer Institute (NCI, US) catalogue, ComGenex catalogue (Budapest, Hungary), Asinex (Moscow, Russia) etc. Compounds are selected based on their ability to bind to functionally important regions of the 30S ribosomal subunit as predicted by computer docking programs as defined herein.

The term "comparing a structure" refers to the process of superimposing the electron density map of the 30S ribosomal subunit bound by a candidate modulator compound with the electron density map obtained with a 30S ribosomal subunit in the absence of the candidate modulator compound.

The term "characterizing an active site" refers to defining those residues of the 30S subunit that participate in, for example (1) the binding of a candidate modulator compound to the 30S ribosomal subunit; (2) tRNA binding; (3) mRNA binding; (4) polypeptide synthesis or (5) translocation. The structural components of active sites can include regions of the 30S ribosomal complex not directly associated with tRNA or mRNA or modulator compound binding but which are required for the ribosome to function, for example those regions which undergo structural changes associated with protein synthesis or are target sites for regulation by cofactors, phosphorylation or acetylation.

The term "difference Fourier electron density maps" refers to the electron density map obtained by subtracting the X-ray crystallographic diffraction data of the 30S ribosomal subunit in the presence of ligand from the X-ray crystallographic diffraction data of the 30S subunit in the absence of ligand.

The term "modelling the structure" refers to the examination of the interaction of 30S subunit binding partners and the known three dimensional structure of the 30S ribosomal subunit using docking programs such as GRAM, DOCK, or AUTODOCK [Dunbrack et al., Folding & Design, 2:27-42 (1997)]. Appropriate modification of the shape or chemical structure of a potential modulator can improve binding specificity and minimize repulsion and steric hindrance between the 30S subunit and the modulator.

The term "analyzing a 30S ligand complex" refers to the determination of 30S-ligand complex structure by defining the difference Fourier electron density maps as described herein.

The term "computer fitting model" refers to computer programs that are used to alter the structure of a candidate modulator compound so that it can bind stably and specifically and with minimal interference to a defined active site of the 30S ribosomal subunit.

The term "docking program" refers to computer software programs that are used to predict the structure of a 30S-ligand complex. A number of docking programs can be used (Jones, G. and Willett, P. (1995). Docking small-molecule ligands into active sites. Curr Opin Biotechnol, 6(6), 652-6.), for example, AutoDock is a suite of automated docking tools that are designed to predict how small molecules, such as substrates or drug candidates, bind to a receptor of known 3D structure. An alternative program, the Global RAnge Molecular Matching (GRAMM) methodology, relies on an empirical approach to smoothing the intermolecular energy function by changing the range of the atom-atom potentials. The technique locates the area of the global minimum of intermolecular energy for structures of different accuracy. The quality of the prediction, however, depends on the accuracy of the structures.

The term "activity of a binding partner" refers to the ability of a binding partner to increase or decrease the translational activity of a ribosome containing a 30S ribosomal subunit by at least 10% when bound to the 30S ribosomal subunit as compared to the translational activity of a ribosome containing the 30S ribosomal subunit in the absence of binding partner.

The 30S Crystal Structure.

The high resolution structure provided herein provides a crystal with unit cell dimensions which are provided in the accompanying table 1 to 3 decimal places, i.e. a=b=401.375, c=175.887 Å. However, those of skill in the art wishing to reproduce the crystallization described herein and obtain such crystals will appreciate that a degree of experimental variability and error will mean that crystals of the invention will be obtained with a unit cell dimension within, but not exactly corresponding to, this size. Thus, crystals of the invention may generally be defined as having unit cell dimensions of a=401.4±about 4.0 Å, b=401.4±about 4.0 Å, c=175.9±about 5.0 Å, preferably a=401.4±about 1.0 Å, b=401.4±about 1.0 Å, c=175.9±about 2.0 Å, preferably a=401.4±about 0.7 Å, b=401.4±about 0.7 Å, c=175.9±about 1.4 Å, and more preferably a=401.4±about 0.2 Å, b=401.4±about 0.2 Å, c=175.9±about 0.4 Å. These unit cell sizes are believed to define a novel and more highly resolved unit cell size than has previously been possible in the art.

Table 1.

The coordinates of Table 1 provide a measure of atomic location in Angstroms, to a third decimal place. In order to use the information in these Tables for the purposes described herein as being aspects of the present invention, these coordinates may be varied by up to about ±1.0, such as by up to about ±0.7, preferably no more than up to about ±0.5 Angstroms, without departing from the scope of the invention.

Furthermore, varying the relative atomic positions of the atoms of the structure so that the root mean square deviation of the 16S RNA or S2-S20 protein backbone atoms is less than about 1.5 Å (preferably less than about 1.0 Å and more preferably less than about 0.5 Å) when superimposed on the coordinates provided in Table 1 for these structures, will generally result in a structure which is "substantially the same" as the structure of Table 1 in terms of both its structural characteristics and potency for structure-based drug design of 30S ligands.

Thus for the purposes described herein as being aspects of the present invention, it is within the scope of the invention if: the Table 1 coordinates are transposed to a different origin and/or axes; the relative atomic positions of the atoms of the structure are varied so that the root mean square deviation of conserved residue backbone atoms is less than about 1.5 Å (preferably less than about 1.0 Å and more preferably less than about 0.5 Å) when superimposed on the coordinates provided in Table 1 for the conserved residue backbone atoms; and/or the number and/or positions of water molecules is varied. Reference herein to the use of the coordinates of Table 1 thus includes the use of coordinates in which one or more individual values of the Table are varied in this way.

Table 1 includes coordinates of two zinc ions, together with 202 other ions which are not identified, which, while not wishing to be bound by any one theory, are believed to be selected from cobalt and magnesium. Some or all of these ions may optionally be discarded from Table 1 when using the data. The table also lists the coordinates of a 26 amino acid peptide, Thx, as well as a 6 nucleotide fragment of mRNA, NNNUCU, designated as molecule X. Both the coordinates of both these molecules may likewise optionally be discarded, i.e. so that the coordinates of the 16S RNA and the proteins S2 to S20 alone are modelled and used in applications of the invention.

There are a few N- or C-terminal sequences of the S2 to S20 proteins which were not resolved in the structure of Table 1, together with a some of the 5' and 3' residues of the 16S RNA. These are not essential for the purposes of the present invention, but are listed in Table 2 for completeness. Those of skill in the art may, if desired, wish to adapt the structures provided by the coordinate of Table 1 by modelling in one or more of the amino acids or nucleotides of Table 2.

This methodology provides those of skill in the art a means to provide 30S crystals of T. thermophilus. The conservation of ribosome structure, particularly regions of structure essential for function, between prokaryotes, for example prokaryotes which are human pathogens, such as Staphylococcus spp, and the like, allows the structure herein to be useful in the provision of anti-bacterial agents in general. Thus, the structure may be used to solve 30S subunits by the technique of molecular replacement. In such a method, x-ray diffraction data are obtained from crystals of a 30S subunit from another species, e.g. a species of a bacteria pathogenic to humans. The coordinates of Table 1 may be used to find the orientation of the unknown molecule in the crystal, and electron density maps calculated. These maps can then be interpreted with the sequence of the species in question, and the coordinates of the 30S structure described herein can be used to help and speed interpretation. In this way, the structure of the 30S subunit crystal of the invention facilitates the determination of structures of 30S subunits and whole ribosomes from other organisms.

Accordingly, the invention provides a method for the determination of the structure of a bacterial 30S from a species other than T. thermophilus which method comprises:

(a) crystallising the 30S of the species to obtain a crystal;
(b) performing X-ray crystallography on the crystal to obtain X-ray diffraction data;
(c) providing the structure data of Table 1; and
(d) using molecular replacement to calculate an electron density map of the 30S.

In such a method, the 30S may be prepared by removal of the S1 subunit, as described herein.

The electron density map obtained may then be used to calculate the atomic coordinate data of the 30S. The atomic coordinate data thus obtained may be used to for the design and analysis of new and specific ligands for 30S as described herein.

Production of Crystals.

Selective removal of the S1 subunit protein facilitates the generation of crystals according to the invention. A suitable method for the selective removal of the S1 subunit protein involves the use of a hydrophobic interaction chromatography column (poros-ET). 30S ribosomal subunits lacking the S1 subunit may suitably be separated from those containing the S1 subunit by running a column using a reverse ammonium sulfate gradient from 1.5M to 0.5M, with 20 mM Hepes, pH 7.5, and 10 mM acetate. The 30S subunits lacking S1 are eluted first, giving the first major peak. During elution of the 30S peak the ammonium sulfate concentration is maintained at a constant level. Once the 30S peak has eluted the ammonium sulfate concentration is then further reduced to elute the 30S+S1 fraction.

An alternative method for the selective removal of the S1 subunit protein is by preparative gel electrophoresis. Gel electrophoresis may suitably be carried out by first preparing and mixing a 3% acrylamide, 0.5% agarose cylindrical gel, and pouring this gel into a BioRad Prep Cell. 30S ribosomal subunits are then loaded onto the gel and continuously eluted as they emerge form the other end of the gel. The 30S fraction lacking the S1 subunit comes off first, giving the first major peak. The 30S+S1 fraction gives the trailing peak (or shoulder) and can be discarded.

Selective removal of the S1 ribosomal subunit can also be achieved by poly-U sepharose chromatography followed by extensive salt washing as described in A. R. Subramanian, Rienhardt, P., Kimura, M. and Suryanarayana, T. (1981): Fragments of Ribosomal Protein S1 and its mutant Form m1S1: Localization of Nucelic Acid Binding Domains in the Middle Region of S1. Eur. J. Biochem. 119, 245-249 and B. Subramanian, A. R., (1983): Structure and Functions of Ribosomal Protein S1. In Progress in Nucleic Acid Research and Molecular Biology, v. 28, W. E. Cohn, (ed.) 101-142. Academic Press, New York. (described on page 104).

Once the S1 is removed, the crystals may be formed, using suitable conditions. These include the use of 13-17% v/v methyl-2,4-pentanediol in the presence of 200-300 (e.g. about 250) mM KCl, 50-100 (e.g. about 75) mM ammonium chloride, 15-30 (e.g. about 15 or about 25) mM $MgCl_2$ at a pH of 6.0-7.5 (e.g about pH 6.3-6.7 such as pH 6.5) in 50-150 (e.g. about 100) mM sodium or potassium cacodylate or MES (2-(N-morpholino)ethane sulphonic acid).

In a particular aspect, the conditions may comprise the use of 250 mM KCl, 75 mM $NH_4Cl$, 25 mM $MgCl_2$, 6 mM 2-mercaptoethanol in 0.1 M potassium cacodylate or 0.1 M MES (2-N-morpholino-ethanesulfonic acid) at pH 6.5 with 13-17% MPD as the precipitant.

The crystals may be grown by any suitable method known as such to those of skill in the art. Suitably, the crystals may be grown over a period of 4-8 weeks at about 4° C. The structure of the crystals so obtained may be resolved, and crystals which resolve to a resolution of at least about 3 Å selected. Crystals which resolve to a resolution of at least about 3 Å obtainable by such a method are a further aspect of the invention.

Uses of Structural Data of Table 1.

The determination of the three-dimensional structure of 30S provides a basis for the design of new and specific ligands for 30S. For example, knowing the three-dimensional structure of 30S, computer modelling programs may be used to design different molecules expected to interact with possible or confirmed active sites, such as binding sites or other structural or functional features of 30S.

Modelling of Candidate Compounds

The high resolution model of the 30S provided by Table 1 may be used to examine and determine the binding of antibiotics known to target this ribosome subunit. Such antibiotics include paromomycin, streptomycin, spectinomycin, tetracycline, pactamycin and hygromycin B.

A candidate ligand, particularly but not necessarily one which acts as an inhibitor molecule, may be any available compound. A number of commercial sources of libraries of compound structures are available, for example the Cambridge Structural Database, the Chemical Directory (ACD) from the company MDL (US) as well as various electronic catalogues of publicly available compounds such as the National Cancer Institute (NCI, US) catalogue, ComGenex catalogue (Budapest, Hungary), Asinex (Moscow, Russia) etc. Such libraries may be used to allow computer-based high throughput screening of many compounds in order to identify those with potential to interact with the active site of a ribosome.

More specifically, a potential ligand capable of modulating 30S activity can be examined through the use of computer modelling using a docking program such as GRAM, DOCK, or AUTODOCK (see Walters et al., *Drug Discovery Today*, Vol. 3, No. 4, (1998), 160-178, and Dunbrack et al., *Folding and Design*, 2, (1997), 27-42) to identify potential ligands of 30S. This procedure can include computer fitting of potential ligands to 30S or a subdomain thereof to ascertain how well the shape and the chemical structure of the potential ligand will bind to the enzyme.

Also computer-assisted, manual examination of the active site structure of 30S may be performed. The use of programs such as GRID (Goodford, *J. Med. Chem.*, 28, (1985), 849-857)—a program that determines probable interaction sites between molecules with various functional groups and the enzyme surface—may also be used to analyse the active site to predict partial structures of ligands for the site.

Computer programs can be employed to estimate the attraction, repulsion, and steric hindrance of the two binding partners (e.g. the 30S and a potential ligand). Generally, the tighter the fit, the fewer the steric hindrances, and the greater the attractive forces, the more potent the potential ligand since these properties are consistent with a tighter binding constant. Furthermore, the more specificity in the design of a potential ligand, the more likely it is that the ligand will not interact with other proteins as well. This will tend to minimise potential side-effects due to unwanted interactions with other proteins.

Having designed or selected possible binding ligands, these can then be screened for activity. Consequently, the method preferably further comprises the further steps of:

(a) obtaining or synthesising the potential ligand; and (b) contacting the potential ligand with 30S to determine the ability of the potential ligand to interact with 30S.

More preferably, in latter step the potential ligand is contacted with 30S under conditions to determine its function, for example in a cell free translation system. Such conditions (including cell free translation systems) are known in the art.

Instead of, or in addition to, performing such an assay, the method may comprise the further steps of:

obtaining or synthesising the potential ligand;

forming a complex of 30S and the potential ligand; and analysing the complex by X-ray crystallography to determine the ability of the potential ligand to interact with 30S. Detailed structural information can then be obtained about the binding of the potential ligand to 30S, and in the light of this information adjustments can be made to the structure or functionality of the potential ligand, e.g. to improve binding to the active site. These steps may be repeated and re-repeated as necessary.

Another aspect of the invention includes a compound, which is identified as a ligand of 30S by the method of the above aspects of the invention.

The present high-resolution structure of 30S provides a means to determine the location of binding of antibiotics, as well as the interactions at the location(s) between 30S and the antibiotic. Such antibiotics include paromomycin, streptomycin spectinomycin, tetracycline, pactamycin and hygromycin B. The high-resolution structure of Table 1 may be used to model the binding to 30S of these, other antibiotics and other ligands. Thus, in another aspect, the invention provides a method of analysing a 30S-ligand (wherein "ligand" includes, but is not limited to, an antibiotic) complex comprising the steps of (i) cocrystallising the 30S with the ligand or soaking the ligand into crystals of the 30S; (ii) collecting X-ray crystallographic diffraction data from the crystals of the 30S-ligand complex and (iii) using the three-dimensional structure of 30S of Table 1, or at least one sub-domain thereof, to generate a difference Fourier electron density map of the 30S-ligand; and (iv) modelling the ligand in the difference Fourier electron density.

Therefore, 30S-ligand complexes can be crystallised and analysed using X-ray diffraction methods, e.g. according to the approach described by Greer et al., *J. of Medicinal Chemistry*, Vol. 37, (1994), 1035-1054, and difference Fourier electron density maps can be calculated based on X-ray diffraction patterns of soaked or co-crystallised 30S and the solved structure of uncomplexed 30S. These maps can then be used to determine the structure of the ligand bound to the 30S and/or changes the conformation of 30S.

Data obtained from a ligand bound to 30S may be used to improve the ligand, for example by adding or removing functional groups, substituting groups or altering its shape to obtain improved candidates, which may then be screened, solved in complex as described herein above, in an iterative process.

Electron density maps can be calculated using programs such as those from the CCP4 computing package (Collaborative Computational Project 4. The CCP4 Suite: Programs for Protein Crystallography, *Acta Crystallographica*, D50, (1994), 760-763.). For map visualisation and model building programs such as "O" (Jones et al., *Acta Crystallograhy*, A47, (1991), 110-119) can be used.

By providing such computer readable media, the atomic coordinate data can be routinely accessed to model 30S or a sub-domain thereof. For example, RASMOL is a publicly available computer software package, which allows access and analysis of atomic coordinate data for structure determination and/or rational drug design.

On the other hand, structure factor data, which are derivable from atomic coordinate data (see e.g. Blundell et al., in *Protein Crystallography*, Academic Press, New York, London and San Francisco, (1976)), are particularly useful for calculating, e.g., difference Fourier electron density maps.

In another aspect, the present invention provides systems, particularly computer systems, intended to generate structures and/or perform rational drug design for 30S and/or 30S ligand complexes, the systems containing either (a) atomic coordinate data according to Table 1, the data defining the three-dimensional structure of 30S or at least one sub-domain thereof, or (b) structure factor data for 30S, the structure factor data being derivable from the atomic coordinate data of Table 1.

Mutant strains resistant to the action of these antibiotics can arise through mutation of a protein subunit of the 30S or through mutation or modification in the 16S RNA (e.g. 2'O-methylation), or modification (e.g. acetylation) of the antibiotic). The sites of mutations in some cases are known or can be identified. Where such sites are identified through, for example, primary sequence data, the invention provides a means to model the structure of the mutants.

There is thus provided a method which comprises providing the structure of the 30S ribosome of Table 1, changing one amino acid or nucleotide of the structure to provide a mutant 30S, and modelling the structure of the mutant 30S to provide a structure of the mutant. The mutant may be used in the manner described above for the wild type, e.g. stored in computer readable form, modelled to provide ligands, and the like. The modelling may be based upon the predicted behaviour of the atoms of the changed amino acid based upon its interaction with the surrounding atoms in the model provided herein.

This process may be iterative, e.g. to produce successive mutations into the 30S structure, for example 2, 3, 4, or 5 to 10 mutations or more.

Regions of 30S which may be subject to this aspect of the invention include but are not limited to those regions identified in the accompanying examples as regions of the 30S involved in ribosome function.

In a further aspect, the present invention provides a means to solve or interpret electron density maps of the whole 70S ribosome at low or high resolution, and thus solve the structure of the whole 70S ribosome.

In particular, the invention provides a method for the determination of the structure of a bacterial 70S ribosome, which method comprises
(a) crystallising the 70S of the species to obtain a crystal;
(b) performing X-ray crystallography on the crystal to obtain X-ray diffraction data;
(c) providing the structure data of Table 1; and
(d) using molecular replacement to calculate an electron density map of the 70S.

The invention is illustrated, but not limited, below by the following examples and their accompanying Figure and Tables. In Table 1 there is shown in each row Atom number, element type, residue (amino acid, nucleotide, etc.), number in molecule (for proteins N to C terminal direction, for nucleic acid 5' to 3' direction), X, Y and Z co-ordinates, occupancy, B factor ($Å^2$) and an identifier for the member of the 30S (e.g. for the subunits in the format "ASn" where A is an arbitrary letter, different for each member, S is the subunit and n is the subunit number; and for the 16S as "A16S").

Throughout the accompanying example, the numbering system for *E. Coli* 16S RNA is used as well as the standard helix numbering, denoted H1-H45, for the secondary structure elements [19] with some modifications as shown in FIG. 1. The most significant differences between the *E. Coli* and *T. thermophilus* sequences are a shorter H6 and H10, and insertions in H9 and H33a. Any insertions in *T. thermophilus* relative to *E. coli* are indicated in the coordinates with an insertion letter after the nucleotide number, following the practice for tRNA.

Crystallization of the 30S, Data Collection and Structure Determination.

This example discloses the procedures used to generate 30S ribosomal subunit crystals, collect X-ray diffraction data and enable structure determination.

Crystallization of the 30S 30S crystals completely lack ribosomal protein S1. S1 was, therefore, selectively removed from the 30S ribosomal subunit prior to crystallization. Crystals were obtained in 13-17% MPD over a range of pH in the salt and magnesium conditions described by Trakhanov et al [3]. The crystals were largest and most reproducibly obtained at a pH of 6.5 in 0.1 M cacodylate or MES buffer. Crystals took approximately 6 weeks at 4° C. to grow to their maximum size. The largest crystals, which were required for high resolution data collection, grew to a size of 80-100×80-100×200-300 microns. The activity of redissolved crystals in poly(U)-directed protein synthesis was comparable to that of freshly isolated 30S subunits.

Data Collection

Crystals were transferred to 26% MPD by vapor diffusion in two steps over a period of 6 days. All crystals (except for those soaked in osmium hexammine or osmium pentammine) also contained 1 mM cobalt hexammine in the cryoprotectant. Crystals were flash-cooled by plunging into liquid nitrogen, and data collection was done in a cryostream at 90-100 K.

A large fraction of crystals was screened at beamlines 9.6 or 14.1 at the SRS at Daresbury Laboratories, using two short exposures at least 40 degrees apart. These crystals were then analyzed for diffraction limits, cell dimensions and mosaic spread. Only crystals of similar cell dimensions and with reasonable mosaic spread were used for data collection.

Potential derivatives were screened on beamlines X25 at the NSLS at Brookhaven National Laboratory and BM-14 at the ESRF (Grenoble). Data to about 4.5 Å were obtained from X25. High resolution data were collected at SBC ID-19 at the APS in Argonne National Laboratory, and ID 14-4 at the ESRF. In all cases, derivative data were collected at the peak of the fluorescence at the LIII edge to maximize anomalous differences. At X25 and SBC ID-19, the kappa goniostat was used to rotate precisely about a mirror plane so that small anomalous differences could be measured accurately. Each crystal typically yielded 3-10 degrees of data. Data were integrated and scaled using HKL-2000 [10].

Structure Determination

Previously determined phases at 5.5 Å [9] were used to locate heavy atom sites using anomalous difference Fourier maps. Initially, these sites were used for phasing to 3.35 Å using the program SOLVE [11], followed by density modification with SOLOMON [12], using the procedure implemented in SHARP [13]. Optimization of the various parameters in the procedure was required to obtain interpretable maps. The RNA and some of the proteins were built using the SOLVE maps. The sequence of *Thermus thermophilus* 16S RNA [14] was used for the structure. For proteins, a combination of previously published sequences and new ones from the Gottingen *Thermus* genome sequencing project were used. Improved maps were obtained by calculating experimental phases to 3.2 Å using SHARP followed by density modification and phase extension to 3.05 Å with DM [15]. The improved maps allowed us to build all the ordered parts of the structure. The model was built using O [16], and refined using the program CNS [17]. Maximum likelihood refinement was used, initially with both amplitudes and experimental phase probability distributions to 3.35 Å, and subsequently with amplitudes to 3.05 Å.

The 30S subunit from *Thermus thermophilus* consists of a 1522 nucleotide 16S ribosomal RNA [14] and 21 associated proteins, of which 20 have known counterparts in *E. coli*. Protein S21 is not present in *Thermus*, and protein S1 has been removed from the 30S prior to crystallization. In addition, a 26 residue peptide, Thx, is present in *Thermus* 30S subunits [18].

Experimentally phased maps clearly showed main chain density for RNA and protein, individual bases (which were often of sufficient quality to distinguish purines from pyrimidines), and large well-ordered side chains of proteins. These maps were used to build 16S RNA and the previously unknown proteins S2, S3, S9, S10, S11, S12, S13, S14 and Thx. In addition, regions that were disordered in isolated structures or had changed significantly were also built. This often consisted of significant portions of the N- and C-terminal tails of the proteins, sometimes including entire domains that were unfolded in isolation. Proteins with small cores and long loops, such as S16 and S17, had to be substantially rebuilt, since these loops were generally disordered in the solution NMR structures. Finally, the entire structure was rebuilt after an initial round of refinement. The current model consists of nucleotides 5-1511 of *Thermus thermophilus* 16S RNA (corresponding to 5-1534 of *E. coli* 16S RNA) and all of the ordered regions of the associated 20 proteins. The current model has been refined against 3.05 Å data with a conventional R-factor of 0.213, a free R-factor of 0.256 and good geometry. For the proteins, 94% of the residues were in the core or allowed regions of the Ramachandran plot, 3.9% in the generously allowed region and 1.8% in the disallowed region.

Structure of 16S RNA

The secondary structure of 16S ribosomal RNA contains forty-five double helices connected by short single-stranded segments. In the crystal structure, many of these helices are coaxially stacked with a helix neighboring in the sequence. There are 13 groups of coaxially stacked helices and 23 unstacked helices in 16S rRNA, for a total of 36 helical elements. There are three different types of helix-helix packing. Most of the helical elements are packed in a minor groove to minor groove fashion, which often requires distortions from canonical A-form helical geometry in one of the two helices. Adenosines from internal loops or from hairpin loops often mediate docking against an A-form double helix, with a dense network of base-2' OH and 2' OH-2' OH hydrogen bonds stabilising the packing. Less often, helix-helix packing occurs in a different mode, by insertion of a ridge of phosphates into a complementary minor groove of another helix. This packing mode is stabilized by hydrogen bonds between the ridge of phosphate oxygens and a layer of 2' OH and guanine base $NH_2$ groups. These guanine N2 groups are often made more accessible by the geometry of G-U pairs, which places this moiety farther into the minor groove than do Watson-Crick pairs. Finally, the rare end-on mode of interhelical packing uses a purine base to mediate the perpendicular packing of one helix against the minor groove of another helix. All three modes of helix-helix packing are further stabilized by idiosyncratic interactions between double-helical RNA and short non-helical RNA segments. Small bulges of one to three nucleotides are often found to pack either between helices or in the major groove of a helix.

Structure of 5' Domain (fpd)

The fpd of 16S RNA contains 19 double helices, arranged as 7 groups of coaxially stacked helices and 5 unstacked helices, for a total of 12 double-helical elements packed tightly together. The result is a wedge-shaped mass of RNA that tapers to a single layer of double helices near the top of the domain. Like the other domains, the fpd is rather longer along the subunit interface than in the perpendicular direction.

The fpd can be divided into three subdomains, roughly corresponding to the upper, lower, and middle thirds of the secondary structure of the fpd. These subdomains make up the top and left-hand, the middle, and the lower right-hand sides of the body, respectively, in the view from 50S. The upper subdomain is a nearly planar arrangement of four helical elements (H16/H17, H4/1H15, H1/H3, and H18). The H16/H17 stack forms the left-hand border of the body as viewed from 50S. This stack is almost 120 Å long, with H16 making contact with the head and H17 reaching the bottom of the subunit. Internal loops in both helices contain S-turns, which are used to modulate the position of the phosphate backbone in the case of H17, or to create an extended minor groove surface for helix-helix docking in the case of H16. The H4/H15 stack points towards the bottom of the subunit, with H15 well-packed against H17. The H1/H3 stack is bent by the conserved bulge at position 31, which results in the proximal end being horizontal and the terminal end pointing up to the head. The fourth helical element is H18, which is sharply bent to accommodate the 530 pseudoknot, defined by the unstacked helices 505-507/524-526 (H18.2) and 521-522/527-528 (H18.1). H18 is well-packed between the other two upwards-pointing elements of the upper subdomain, H1/H3 and H16. The 530 pseudoknot packs against the central pseudoknot at the H18.1-H1 interface.

The middle subdomain contains four helical elements (H5, H6, H12/H6A, and H13/H14) that form a layer between the upper and lower subdomains in the centre of the body. There are relatively few packing interactions within the subdomain, and several of its helices pack against the upper subdomain on one side and the lower subdomain on the other. Thus, at the bottom of the subunit, the conserved root of H6 packs against H8 (lower subdomain) on one side and H15 (upper subdomain) on the other side. Similarly, the H12/H6A stack packs against H4 (upper subdomain) and H7 (lower subdomain). H12/H6A also packs against H5 and the 117 loop, which pack against elements from the upper and lower subdomains, respectively. H5 is well-packed against H15 and the 117 loop stacks with the root of H11. H5 also packs against the H13/H14 stack in the phosphate ridge-minor groove manner. H13/H14 interacts with two different regions of the lower subdomain. The conserved UACG hairpin loop at the end of H14 packs against the 160 GAAA hairpin from H8 while the large conserved hairpin at the end of H13 interacts with H7. This hairpin loop also makes many interactions with elements from the middle subdomain.

The lower subdomain is a collection of three helical elements that form an open saddle-shaped structure in the lower right-hand corner of the body. The H8/H9 stack stretches from the back of the subunit to the front, with the conserved 160 GAAA hairpin pointing toward the 50S subunit. It packs tightly against the H7/H10 stack at the 4-way junction that joins them, and again at a *Thermus*-specific interaction between insertions at nucleotides 190 and 129. The H7/H10 stack also makes weak interactions with H15 and H17 from the upper subdomain at the bottom of the subunit. H11 contains two sharp bends that allow its conserved terminal hairpin loop to pack against H7. Both bends are stabilized by short-range minor-groove to minor-groove packing contacts.

Structure of the Central Domain (cd)

The cd is the RNA component of the platform. Its fold based on the previous 5.5 Å structure [9] is in excellent agreement with the current structure. It contains nine helical elements folded into a W-shape in the 50S view. Two long single-stranded segments of RNA, the 570 and 820 loops, are also important structural elements. The domain is dominated by the long stack of H21/H22/H23, which forms the U-shaped perimeter of the domain. H21 is the only component of the left-hand arm of the W, while H22 and H23 form the base of the right-hand side. The right-hand arm of the W consists of $H_{23}B$ and H24A whose conserved hairpin loops are tightly packed. This arrangement requires sharp bends between H23 and $H_{23}B$, and between H24 and H24A. The $H23/H_{23}B$ bend is stabilized by short-range minor groove-minor groove packing interactions. The H24/H24A bend is more unusual in that the bend is towards the major groove, which places a ridge of H24A phosphates in the major groove of H24. This major-groove bend is stabilized partly by short-range base-base and base-backbone interactions in the major groove of the bend, and partly by long-range interactions between the bent H24/H24A minor groove and the minor groove of H23. The heart of the central domain is the thicker middle arm of the W, which contains six helical elements (H20, H19/H25, H24, H26/H26A, H27, and H23B) and the 570 and 820 loops. On the left-hand side of the arm, the H26/H26A stack packs tightly against H22, the base of H25, and the 570 loop. The H25/H19 stack packs well with H20 and with the 570 loop. On the right-hand side of the central arm of the W, H23A packs well with H22, the 820 loop stacks on H24, and H24 packs well with the conserved GCAA hairpin loop of H27. In the centre of the arm, H23A packs with H26 in the phosphate ridge-minor groove manner, and the conserved H23A GAAG hairpin loop packs against H20. The 820 loop also interacts with H20, H25, and the 570 loop.

Structure of the 3' Major Domain (tmd)

The 3' major domain (tpd) is the RNA component of the head of the 30S subunit. From the 50S view, the left-hand side of the head tapers to a beak made of RNA on the 50S side and protein on the solvent side. Like the other domains, the tpd is relatively thin in the direction perpendicular to the intersubunit interface. The tpd consists of fifteen helical elements, most of which do not stack on a neighboring helix, in contrast to the extensive stacking of neigboring helices seen in the fpd and the central domain. The tpd can be divided into three subdomains, which correspond to the upper, middle, and lower portions of the tpd secondary structure. The upper subdomain is an extended structure in the part of the head farthest from the 50S subunit, and makes relatively few packing contacts with RNA from the other head subdomains. The lower and middle subdomains are more globular and are more intimately packed together, and make up the front-right and front-left portions of the head, respectively. The middle subdomain includes the RNA portion of the beak.

The upper subdomain contains three helical elements that make up a well-separated structure on the solvent side of the head. The subdomain is dominated by the H35-H36-H38-H39 stack, which stretches from the top to the bottom of the head. The other two helical elements of this subdomain are H37 and H40, which pack well with each other and loosely with the H35-H36-H38-H39 stack. The H37-H40 pack is mediated by a semiconserved GAAA hp in H40 with adjacent G-C pairs in H37.

The smaller middle subdomain is extended and contains only four helical elements, H32, H33/H33A, H33B and H34. Two of these (H33/H33A and $H_{33}B$) form the Y-shaped RNA component of the beak. The H33/H33A stack points to the left in the 50S view while $H_{33}B$ points to the right, with its terminal conserved GNRA hairpin loop packed against H32, the covalent connection between the beak and the lower subdomain. H32 in turn packs against the H33-H34 junction as well as the 980 loop in the lower subdomain. With the exception of a small packing interaction with H32, the irregular H34 makes only long-range and somewhat tenuous packing interactions. The first is with H31 in the lower subdomain, an unusually weak minor-groove to minor groove packing. The second interaction is an unusual end-on packing interaction with the minor groove of the H34/H35/H38 junction in the upper subdomain.

The lower subdomain contains almost half of the tpd RNA and contains seven helical elements (H28/H29, H30, H31/980 loop, H41, H41A, H42 and H43) intimately packed into a globular mass. Helices 42 and 43 are arranged in an approximately parallel fashion at the centre of the fold, and each interacts with at least three of the other helical elements. Helices 42 and 43 dock together by means of a minor-groove to minor-groove packing of their conserved hairpin loops. On the solvent side of the H42/H43 pair, H41 packs with both H42 and H43, while the terminal GCAA hairpin loop of H41A packs against H42. This arrangement requires a sharp bend between H41 and H41A, whose minor grooves pack against each other at the bend. The H43-H41 pack is made more extensive by an underwound A-rich internal loop in H41. On the 50S side of the central H42/H43 pair are H29, H30, H31 and the 980 loop. H43 is well-packed with H29 and makes weaker interactions with H30 and the 980 loop, while H42 is well-packed with H30 and the 980 loop. The H42-H30 pack is mediated by successive conserved G-A pairs at the base of H42. The H43-H29 pack is mediated by a conserved S-turn at the base of H43. An S-turn also mediates the packing of H42 with H41. H31 is a peripheral element of the subdomain, packing well only with H30, but also packs with H34 from the middle subdomain.

Structure of the 3' Minor Domain

The 3' minor domain consists of just two helices at the subunit interface. H44 is the longest single helix in the subunit, and stretches from the bottom of the head to the bottom of the body. It projects prominently from the body for interaction with the 50S subunit. H45 is approximately perpendicular to H44, with its conserved GGAA hairpin loop packed against H44 and available for interaction with the large subunit.

Interaction of 30S Ribosomal Subunit Proteins with 16S RRNA

The current structure includes all of the 30S proteins except S1. The proteins generally consist of one or more folded domains, about half of which were known from previous work on isolated proteins. However, nearly all of the proteins contain extended termini or loops which interact intimately with RNA and were disordered in the isolated structures. Although most of the proteins form intimate contacts with ribosomal RNA, there are also protein-protein interactions such as those seen in the S4-S5-S8 and S3-S10-S14 clusters.

Proteins in the Central Domain (S18, S11, S8, S15)

S18: S18 in the 30S consists of residues 19-88. It consists of two helices, and a third helical element formed by two short turns from different parts of the structure that stack end-to-end. These helices together form a hydrophobic core. The C-terminus interacts with S11.

S11: S11 is a new structure and consists of two helices packed against a sheet, a type of fold seen in many ribosomal proteins. The sheet packs against the minor groove of the 690 loop (H23), and has a C-terminal extension that interacts with the C-terminal extension of S118 and also with the 790 loop (H24). Thus, S11 stabilizes folding of the platform, by binding to both H23 and H24 near the tip of the platform.

S8: S8 binds near the H20/H21/H22 three-way junction and makes extensive interactions with H21 and H25. In particular, two loops from S8 (87-92 and 112-118) wrap around the bulged bases 641-642 which were known to be required for high affinity binding of S8 [20, 21]. The N-terminus of the protein also packs against the minor groove of the 825 stem (H25), thus helping the folding of the central domain. Residues K55 on S8 and 653 on RNA are next to each other as would be expected from crosslinking [22]. The extension in *Thermus* S8 of the loop 69-76 packs against S2 from a symmetry related molecule.

S15: S15 binds between H20 and H22 near the three-way junction.

5' Domain Binding Proteins S17, S16 and S20

S17: Although originally thought to be exclusively a 5' domain binding protein, S17 also binds near the H20/H21/H22 three-way junction. The core of S17 is known from NMR to be a β-barrel with an OB fold, with long extended loops [23]. These loops are disordered in solution but bind RNA in the 30S. In *Thermus*, there is a long C-terminal extension to S17 that is organized as an RNA-binding helix. The core of the protein and the C-terminal helix make extensive contacts with H11 and also contact H7. The C-terminal helix also contacts H21 in the central domain. Two long loops, loop 1 (26-36) and loop 2 (60-71) are ordered and interact with disparate domains of RNA exactly as predicted. Loop 1, which contains the site of neamine resistance, is inserted between H21 and a highly irregular structure at the base of H11. The very tip of loop 1 also touches the 560 loop of 16S RNA. Loop 2, which contains the site of a mutant defective in assembly, is involved in stitching together H7 and H11. Thus, S17 interacts with H7, H11 and the 560 loop in the 5' domain, and H21 in the central domain.

S16: For a small protein, S16 has an extensive footprint throughout the 5' domain. All of the residues (1-88) are visible in the electron density, and were rebuilt using an NMR structure 5 [24] as a guide. The protein consists of an N-terminal sheet with two extended loops, and two short helices in the C-terminal end. All of the extensive contacts with 16S RNA are now clear. The β-sheet is packed between the 608/620 internal loop of H21 on one side and a minor groove of H4 on the other. The two loops that extend out from this sheet both interact with RNA. Loop 1 interacts with phosphates in major groove of H4, while residues 39-43 in loop 2 make contact with the phosphate backbone around the internal loop near 453 in H17. The first helix (53-61) also extends across the major groove of this internal loop, while the C-terminal end of the second helix along with the turn leading out of it point into a minor groove of H17. There is also interaction with the 110 loop of the 5' domain. Finally, the extended C-terminus lies across the minor groove at the tip of H17.

S20: The current high resolution structure of S20 shows that the long N-terminal helix contacts the base of H6 and the tip of helix 44, and many conserved basic residues make salt-bridges with phosphates. Helices 2 and 3 of S20 interact with the minor groove of H9, and helix 3 also interacts with tip of H11 (263). Finally the extreme C-terminus of the protein is extended and lies along the minor groove of H9, which is longer in *Thermus* by 11 nucleotides. Thus, S20 brings together several helices near the bottom of the subunit.

Proteins Near the Functional Centre.

S4, S5 and S12 are clustered near the "functional center" of the ribosome and contain the sites of several important mutations.

S4: In the structure of isolated S4 [25, 26] the N-terminal domain was cleaved off prior to crystallization. This N-terminal region is organized as a tightly folded domain with a metal ion (presumably, zinc) that is coordinated by four cysteines. The domain is packed against the body of the protein. While the N-terminus of S4 is highly conserved, the cysteines themselves are not. It is therefore likely that the addition of a "zinc finger" is for additional stability rather than essential for the fold. The linker residues 46-52 connect the N-terminal domain with the rest of the protein. All domains of S4 make intimate contacts with RNA. In particular, S4 makes extensive contacts with a five-way junction where H3, H4, H16, H17 and H18 come together in the 5' domain.

The N-terminal domain is packed against the 420 stem-loop (H16). The largely helical domain I is packed against a complicated region of RNA where H3 and the 507 bulge at the base of H18 come together. The remaining domain of S4 makes extensive contact with the minor groove of the base of H16. In addition, it also makes contact with the tip of the H21, which is itself packed against H4. This position is consistent with the large body of biochemical data on S4 binding to 16S RNA.

The C-terminus of S4 makes an extensive interface with S5. Most of the known mutations of S4 and S5 that confer the ram phenotype are located in this region [27, 28]. The interface consists of several highly conserved salt bridges, and some of the mutations break one or more of these interactions.

S5: The structure of S5 shows that the loop from residues 14-28 is folded back onto the body of the protein in the isolated structure, but is a fully extended β-hairpin in the 30S. Also, the C-terminus of S5, which is disordered in the isolated structure, is mainly helical and packs against a complicated surface of S8 formed by many different strands.

S5 interacts closely with a region of the ribosome where the head and the body come together. In the head, the extended H35/H36 helix packs against H28, which forms the neck of the 30S connecting the body with the head. The tip of H36 makes contact with H26a, H2 and the central pseudoknot in the body. Protein S5 has contacts throughout this region, thereby stabilizing the conformation of the head with respect to the body.

The C-terminal sheet of S5 makes extensive interactions with the major groove of the H1 and the central pseudoknot. The N-terminal domain binds to the major groove of H36, as does the base of the β-hairpin. The tip of the hairpin interacts with the phosphate backbone in H28 and is also very close to H34. Nucleotide 560 is very close to K121 in agreement with crosslinking data.

Most of the extensive interactions with RNA occur via major grooves or phosphate backbone.

S12: S12 is unusual both for its structure and location. It is unique among the 30S proteins in being on the interface side of the subunit. Its central core consists of a b-barrel with an OB fold, a feature found in other proteins such as S17. This core binds together H18, the 530 stem loop (at the tip of H18), H3 and a part of H44 close to the decoding site. An unusual feature is a long extension that connects this core with a short helix at the N-terminus of the protein. This extension threads between the 560 loop and H12 on one side, and H11 on the other, to make contact with both S8 and S17 on the other side of the 30S.

S12 is also the only protein in the vicinity of the decoding site near 1492-1493 of RNA. It is the site of a number of functionally interesting mutations.

The Head Proteins S7 and S9

S7: Protein S7, whose structure in isolation was previously known, is known to be crucial for the assembly of the head [29]. In the 30S structure, the entire sequence is visible, including the very basic N-terminus. S7 binds to a small but complex region of the tpd that encompasses two multiple-stem junctions at a corner of the head. The majority of the interaction surface consists of H29 tightly docked to the S-turn at the base of H43. This docking requires a tight turn at 1346, probably stabilized by S7 binding. Because S7 also makes interactions with H28, its primary surface of interaction encompasses all three of the helices around the H28/H29/H43 three-way junction. The very tight docking of H29 to H43 gives rise to a small region of very high negative charge density, which is bound by a surface of S7 with very high concentration of positive charge (mainly S7 helices 1 and 4).

The second important interaction surface is centred on the second multiple stem junction that S7 binds, the H29/H30/H41/H42 junction. In this junction, H30 and the base of H42 are tightly packed together, with a tight turn between them. An S-turn between helices 41 and 42 mediates packing of H41 and H42, which also have a tight turn between them. H41 also packs very tightly against H43. S7 makes contacts to the phosphate backbone of H41, stabilizing its packing with H43, and to residues around 1240 and 1298 where the tight bends occur in the H29/H30/H41/H42 junction. Contacts with U1240 are particularly intimate: the universally conserved bulge U1240 is deeply buried into a conserved hydrophobic pocket between the 35 and 115 loops of S7.

The β-hairpin is not tightly associated with 16S RNA, but probably fits tightly into the minor groove of the E-site tRNA. The structure is in rough agreement with a model of S7 binding to ribosomal RNA [30], but there are also significant differences, including the location of H43.

S9: S9 consists of a compact RNA-binding domain consisting of 2 helices packed against a 5-stranded sheet, with a third short helix at the C-terminal end of the domain. From this domain, there is a long 25 residue C-terminal tail that snakes into elements of the head RNA. S9 also interacts with S7 via a small hydrophobic patch.

The sheet of S9 makes extensive interactions with H38 and H39. It also has two loops that interact with the 1250 internal loop of H41. The short C-terminal helix interacts with 1177-1180 in H40.

The long C-terminal extension snakes between the H29-H43 junction on one side and the H38-H34 junction on the other to touch a portion of H31.

The S3 S10 S14 Cluster

These three proteins form a cluster on the rear left-hand of the head, as the protein portion of the beak. S3 is clearly stacked on top of the other two proteins, consistent with the order of assembly.

S14: S14 is bound in a crevice in the RNA and is mostly covered by S3 and S10. Almost the whole molecule contacts RNA, including helices H31, H32, H34, H38, and H43. A cross linked residue is in close proximity to the RNA 28.

S14 contains a zinc ion coordinated by four cysteines from a CXXC-X12-CXXC (SEQ ID NO:1) motif. This motif is structurally similar to that found in the first zinc finger in the glucocorticoid receptor. This zinc binding motif is not conserved among all bacteria, although many of the residues surrounding it are, suggesting perhaps that in other organisms the protein folds via a hydrophobic core.

S10: S10 is structurally very similar to the S6 fold, with two helices packed against a 4-stranded sheet. Two of the strands in this sheet are connected by a long β-hairpin that extends out from the sheet and is inserted right into the centre of the head RNA fold. The β-hairpin makes most of the contacts with RNA, including helices H31, H34 and H41. The two strands of the sheet pack into the shallow minor groove of H39, making contacts with backbone residues on both sides of the groove.

S3: S3 contains two domains, both consisting of two helices packed against a 4-stranded sheet, which is similar to several other ribosomal proteins. In addition to the domains there is an N-terminal tail (all of which is visible). The C-terminal 30 residues are poorly conserved and disordered in the structure.

RNA contact is made by the N-terminal tail and the C-terminal domain. The N-terminal tail fits into a major groove of H34. The sheet in the C-terminal domain also packs against H34.

The N-terminal domain makes few if any contacts with the RNA, but is mainly involved with making protein contacts with S10 and S14.

S13 and S19

S13 and S19 form a loose dimer at the very "top" of the interface side of the head, extending both above and closer to the 50S than any of the head RNA. In spite of their location in this flexible region, they are both relatively well-defined in the electron density. Except for the C-terminal tail of S13, which reaches into the head and almost touches the tail of S9, none of these proteins are in contact with any other of the proteins in the small subunit. Together with S12, S11 and S15, these are among the few proteins that surround the region of intersubunit contact.

S13: All 125 residues of S13 are visible in the structure. The N-terminus (about 60 residues) forms a compact domain consisting of three small helices. Of this domain, only a small loop is in contact with the RNA and the domain appears to be clinging to the subunit only by virtue of its highly extended C-terminal region. This region begins with a long, straight alpha-helix that creeps along the top of the 30S head towards S19. It interacts mainly with the 1300 loop and H42. At this point the polypeptide chain bends by about 90 degrees, and the rest of the protein is mostly lacking in any secondary structure. This extended region curves around H41 into the head where it is buried in the RNA about 50-60 Å from the globular, N-terminal domain. It contacts H30 in the head.

S19: S19 consists of 92 residues. An NMR structure of isolated S19 [31] showed a single globular domain consisting of a helix packed against a three-stranded sheet, in which residues 9-78 were ordered. In the 30S structure, residues 2-81 are visible in the electron density. The C-terminus of the protein points towards the interface side and may become ordered in the 70S complex. Like S13, most of the globular domain of S19 is well separated from the RNA, but here both the N- and C-terminal extensions to the globular domain, as well as the loops 68-73 and 34-39 make contacts with H42. The C-terminal extension, like S13, bends around the RNA, to contact H31 while the N-terminus reaches H42 some considerable distance away. Thus, S19 straddles a portion of the head of the 30S. The residues in S13 and S19 that were crosslinked 48 are adjacent to each other in the structure.

S2.

*Thermus* S2 consists of 256 residues of which 7-235 are visible in the structure. The protein consists of a large central domain of about 200 residues that consists of a 5-stranded parallel sheet and four helices connecting them. Two helices that form a small coiled-coil motif protrude out of this domain. The protein is located on the back of the 30S at the interface between the head and the rest of the particle. While it is primarily regarded as a "head" protein, it also makes contacts with the central domain in the structure.

Thx.

This small 26 residue peptide was isolated and characterized from *Thermus* ribosomes [18]. Thx fills a cavity formed by a number of different elements at the very top of the head. Residues 1-24 are visible in the electron density, of which 8-14 form a short helix, flanked by extended ends. It is surrounded by H42, the tip of H41, and the base of H41, while the bottom of the cavity is formed by the major groove of H43. The protein is highly basic, and there are extensive salt-bridges between these residues and phosphates of nearby RNA. Thus, Thx stabilizes a number of different RNA elements that come close together near the top of the head.

Functional Insights from the Structure of the 30S Ribosomal Subunit

During translation of the genetic code, the 30S ribosomal subunit provides the framework for base-pairing between the anticodon of tRNA and the codon of mRNA, and discriminates between cognate and non-cognate tRNAs to ensure translational fidelity, in a process termed decoding. During translocation, the ribosome must move by precisely one codon relative to mRNA and the bound tRNAs. Both decoding and translocation involve "switches" in which precise conformational changes occur in the ribosome. The atomic resolution structure of the 30S subunit allows the interpretation of the environment surrounding the mRNA and tRNA binding sites in molecular terms. In one well-characterized example of a functional switch involved in accuracy, the spatial arrangement of its elements was determined, thus elucidating its architecture. The structure also suggests other possible switching elements in the 30S, and sheds light on the kinds of movements that might occur.

The ribosome contains three tRNA binding sites, designated A (aminoacyl), P (peptidyl) and E (exit), after their respective tRNA substrates. Each site is bipartite, located partly on the 30S ribosomal subunit and partly on the 50S subunit. The A- and P-site tRNAs bind with their aminoacyl acceptor ends on the 50S subunit, and with their anticodon ends base-paired to adjacent mRNA codons on the 30S subunit. The E-site tRNA is bound in a similar orientation, but it is not known whether the E-site tRNA is base-paired to the E-site mRNA codon. The 30S subunit also binds mRNA upstream and downstream of the A, P and E codons. During translation, incoming aminoacyl tRNA is delivered to the A-site as a ternary complex with EF-Tu and GTP. Discrimination of cognate from non-cognate tRNAs occurs in the A-site. It is thought that there is also a second "proofreading" discrimination step in the A-site after GTP hydrolysis by EF-Tu, which is needed to discriminate cognate from near-cognate tRNAs. The 30S P-site has a much higher affinity for tRNA, in order to maintain the reading frame.

There is one well-characterized conformational switch in the 30S subunit, the helix 27 accuracy switch [32]. Genetic and biochemical data support a model in which this switch may be part of a larger-scale conformational change that occurs between initial selection and proofreading of the A-site tRNA, or the switch may play a role in translocation.

Until recently, there has been a large disparity between the high resolution of the genetic and biochemical data that define the RNA components of the active sites of the 30S subunit, and the relatively low-resolution of the three-dimensional structures of ribosomes available. The present invention addresses this disparity. In combination with previous biochemical and other data, it is now possible to identify the detailed structure of 30S active sites. In addition, by superimposing the tRNA and mRNA coordinates from the known 7.8 Å 70S structure, it is now possible to infer many of the interactions between 30S active sites and tRNA/mRNA ligands.

With the complete and high resolution structure of the 30S subunit in hand, it is now possible to identify at the residue level the elements of the 30S subunit that interact with the anticodon stem-loop (ASL) of the A, P and E-site tRNAs and associated mRNA.

Identification of the precise boundaries of the A, P, and E sites in an unbiased fashion in a structure determined in the absence of cognate tRNA ligands would normally be problematic. As it happens, the P-site in the 30S structure is filled with a stem-loop of RNA corresponding to residues 75-95 (in the *E. Coli* numbering system) from the end of the "spur" (H6) of a neighbouring molecule. (Henceforth the term "spur" will refer to the symmetry-related spur docked in the P-site, rather than the spur at the bottom of the same subunit). The spur appears to mimic P-site tRNA by a variety of criteria. The extent of the 30S interaction with the anticodon stem-loop (ASL) is in very good agreement with that determined by affinity measurements [33] and by hydroxyl radical footprinting [34]. Secondly, the conformation of the spur stem-loop is distorted in order to more closely resemble the canonical tRNA ASL conformation [35, 36]: a U-A base pair is broken so that the spur hairpin loop can approximate the conformation of a tRNA ASL, complete with a U-turn and stacked anticodon. Another indication that the spur is a mimic of a bound P-site tRNA ASL is that of the twelve hydrogen bonds between 30S and the spur, only one appears to be sequence-specific, in accordance with the lack of sequence conservation in tRNA anticodon stems. Finally, close contacts of the spur with 16S RNA are on the whole consistent with chemical protection data for P-site tRNA [37] and with the 34-C1400 UV-induced crosslink between tRNA and 16S RNA [38] (the analogous residues are stacked in the 30S crystal structure).

Yet another indication that the spur mimics a P-site tRNA ASL is that its "pseudo-anticodon" is base-paired to a triplet of nucleotides, a mimic of mRNA. A fourth nucleotide is also visible 5' to the pseudo-anticodon, in the E site. These pseudo-codon bases are clearly pyrimidines, and appear to be UCU from the base-pairing geometries, which are U-U, U-C, and U-U since the pseudo-anticodon is UUU. The origin of this "pseudo-message" is unclear, but it probably comes from the 3' end of 16S RNA, which ends with 5' U1542C1543U1544 3'. The last nucleotide of the 16S model is C1533, so that seven disordered nucleotides would span the 25 Å gap between C1533 and U1541, which is clearly stereochemically feasible. Alternatively, it is possible that the 3' end of 16S RNA has been cleaved somewhere between C1533 and U1541 prior to or during crystallization. The presence of functional mimics of mRNA and P-site tRNA also explains why these crystals diffract relatively well: the P-site tRNA makes extensive contacts with both the head and the body of the 30S, thereby helping to lock the particle into a single conformation.

To ask how well pseudomessage and spur mimic mRNA and the ASL of tRNA, the 7.8 Å resolution structure of the 70S ribosome with bound mRNA and tRNAs was used [39]. In that structure, two elements of 16S RNA were identified, H27 and H44. To avoid any possible bias in the interpretation of the spur as a mimic, only H27 and H44 were used in the alignment to superimpose the 70S structures onto the 30S structure. Despite the relatively low resolution of the 70S structure used, a least-squares superposition of these two elements had a phosphate r.m.s.d. of only 2.3 Å. When the 70S elements are superimposed in this manner onto the 30S structure, the P-site tRNA superimposes well onto the 30S spur, and the 30S pseudo-message corresponds to the P-site codon. In particular, the orientation of the spur stem-loop is very similar to the 70S P-site ASL, and there are no significant clashes between the 70S A- and E-site tRNAs and the 30S subunit when superimposed in this manner. It is clear that the spur and pseudo-message cannot be perfect mimics, however, because the pseudo-anticodon—codon helix consists of three pyrimidine-pyrimidine base pairs, which are about 2 Å narrower than Watson-Crick pairs. Thus, it seems likely that the spur and its pseudo-message are good but not perfect mimics of P-site tRNA and P-site codon, respectively, and that the spur mimic model should explain many but perhaps not all features of P-site tRNA binding to the 30S. Moreover, the transformed A- and P-site tRNAs and A-site codon provides a useful landmarks for modeling the extent of the A- and E-sites of the 30S.

The P-Site

The P-site spur contacts several discrete regions of 16S RNA, most of which have been implicated in P-site binding by biochemical experiments. Two proteins also participate in binding the P-site ASL, a possibly surprising result. Most of the contact surface lies between the minor groove of the spur stem and 16S RNA nucleotides 1338-1341, 1229-1230, and the C-terminal tails of proteins S13 and S9. There are many hydrogen bonds between the minor groove (i.e. the 2' OH and base groups) of spur residues C91, C92, and G78 and the minor groove surface of G1338-A1339. Only one of these hydrogen bonds appears to be sequence-specific (G78 N2-A1339 N3). A contact from Lys 126 of S9 appears to help stabilize this minor-groove to minor-groove packing interaction. Both 1338 and 1339 have previously been implicated in P-site binding [37]. A second area of contact, nearly continuous with the first, is between the 16S1229-1230 sugar-phosphate backbone and spur residues G77 and G78. This region of contact is extended by the C-terminal tail of S13, which seems to help glue the spur and the 1229-1230 area together. The other areas of contact are much more tenuous. One interaction is stacking of U82 on C1400, which rationalizes the ASL 34-C1400 uv-induced crosslink [38]. The other is a packing interaction between A790 and spur residues 88-89, with a single hydrogen bond present. A790 is a so-called class III site, that is it is protected by either tRNA or 50S subunits. From the spur interaction, it would thus appear that binding of either the 50S subunit or the P-site ASL stabilizes a contact between A790 N6 and the phosphate of 1498, i.e. a contact between the central and three-prime minor domains. Finally, if the pseudo-codon—pseudo-anticodon helix were a few Å wider, as it would be for a Watson-Crick-paired helix, it would make van der Waals contact with the base of G966. G966 has also previously been implicated as part of the P-site by chemical modification experiments and has also been identified as a one of the few guanines crucial for P-site binding [40].

The P-site codon is threaded through the major groove of the upper portion of helix 44, in a universally conserved region of 16S RNA. There appears to be a tight turn between nucleotides −1 and +1, that is, between the last E-site and the first P-site codon nucleotides. This tight turn is stabilized by a hydrogen bond to the N1/N2 groups of the conserved residue G926, a residue previously implicated as crucial for P-site binding [40]. Additional hydrogen bonds are seen between the 2'OH of +1 to the phosphate of C1498, and between the phosphate of +2 and the 2' OH of C1498. The phosphate of +2 also stacks on the base of C1498. The phosphate of +3 is within hydrogen-bonding distance of two conserved cytidine N4 groups, from C1402 and C1403. The +3 base also stacks on the sugar of C1400. Finally, it appears likely that there are several magnesium ions that may help stabilize the location of the P-site codon in the major groove of H44.

The E-Site

The E-site is defined by the environment surrounding the 70S E-site tRNA superimposed onto the 30S structure, as described above. Unlike the A and P-sites, the E-site consists mostly of protein. Proteins S7 and S11 have a small interface that binds the minor groove of the E-site ASL. The highly conserved beta-hairpin of S7 extends this surface nearly to the bottom of the anticodon, and it is possible that the S7 beta-hairpin helps dissociate the E-site codon from the E-site anticodon. The RNA portion of the E-site makes only tenuous interactions with the E-site ASL. 16S nucleotides 1382 and 1383 may interact with residue 34 of the anticodon. The minor-groove surface of the conserved 16S residues 693 and 694 may interact with the minor-groove surface of the 37-39 residues of the E-site ASL.

The A-Site

The A-site is rather wider and shallower than the P or E sites, perhaps in order to allow rotation of the A-site codon-anticodon helix during or after GTP hydrolysis by EF-Tu. The RNA components of the A-site appear to include portions of the 530 loop, H34 in the head, and residues 1492-1493 from the 3' minor domain, all of which have been previously implicated in A-site binding.

The *Helix* 27 Switch

It is clear that many of the elements that make contact with the various tRNA would have to move during translocation. Indeed, the ribosome is known to undergo extensive conformational changes during the elongation cycle, and these must involve breaking and making precise contacts. However, the precise switching elements in these conformational changes are not known in general, with the exception of a switch in H27.

H27 is proposed to have two alternative base-pairing schemes during translation, one a "ram" or permissive form that pairs 885-887 with 910-912, and an alternative "restrictive" form that pairs 888-890 with 910-912 [32]. The ram form appears to be the more stable form in the ribosome and it features an S-turn (or loop E motif) in H27. The S-turn in H27 is also seen in the tRNA-bound structure of the 70S [39]. A switch to the restrictive form would involve a sliding of the two strands of H27 relative to each other and the S-turn would be replaced by an internal loop with a different structure for H27. Indeed, analysis of the two forms by cryoelectron microscopy reveal noticeable conformational changes in the ribosome, especially around the A-site [41]. Knowledge of the structure surrounding H27 as defined herein together with previous chemical modification data [32] suggest the kinds of movement that are involved in these conformational changes.

The S-turn in H27 around 888 is right next to 1489 in H44, and H27 packs against the minor groove of H44 just below the decoding site. The tip of H27 is close to H11, while 885, which is base-paired with 910 in the conformation, is near both H1 and the 570 loop. Finally, 914 is near both H1 and 526 in the 530 loop. Thus, H27 is right in the heart of an area which includes the decoding site and the 530 loop. So it is not surprising that a change in the conformation of H27 would have affect these elements.

A number of elements that are more accessible in the "restrictive" state appear to be protected in the structure of the present invention. Thus for example, 524-526 are currently base-paired with 507-505 in the 530 pseudoknot. This suggests that the 530 pseudoknot could be broken in the restrictive state. Similarly, 1053 and 1197 are base-paired in the current structure, but they are part of a distorted region of H34 analogous to an S-turn, and it is not hard to envisage that an analogous switch might occur in H34 in the alternative state. Thus, the data in combination with the structure suggests that H34 in the head and the 530 loop in the shoulder move between the two states, with H34 possibly adopting an alternative form, and the 530 pseudoknot being disrupted. In this context, it is interesting to note that both H34 and the 530 loop have been implicated in tRNA binding.

Other parts of the chemical protection data, especially those that are supposed to indicate enhanced accessibility in the ram state, are not so easy to rationalize since they involve protected bases in the structure.

The 30S structure has allowed us to identify details of the tRNA and mRNA binding sites, as well as obtain the first detailed look at the structure around the H27 switch. Clearly, H27 is only one component of major conformational changes that occur during translation. Analysis of the high resolution 30S structure should allow us to identify other potential switching elements, which may then be tested genetically.

EXAMPLES

Example 1

Crystallization of the 30S Ribosomal Subunit

Crystals of *T. thermophilis* 30S ribosomal subunits were obtained by an optimization of the procedure reported by Trakhanov et al. (Trakhanov, S. D. et al FEBS Lett. 220, 319±322 (1987)) with respect to pH and concentrations of $Mg^{2+}$ ions and 2-methyl-2,4-pentanediol (MPD) as described in Wimberly et al. Nature 407, 327-339 (2000). The final conditions were 250 mM KCl, 75 mM $NH_4Cl$, 25 mM $MgCl_2$ and 6 mM 2-mercaptoethanol in 0.1 M potassium caco-dylate or 0.1 M MES (2-N-morpholino-ethanesulphonic acid) at pH 6.5 with 13±17% MPD as the precipitant. 30S crystals completely lacked ribosomal protein S1. Selective removal of the S1 subunit prior to crystallization improved both the crystal size and reproducibility in crystal growth. Typical procedures used to remove the S1 subunit include the use of poly-U sepharose chromatography followed by extensive salt washing as described by Subramanianet et al. Eur. J. Biochem. 119, 245-249 and Subramanian, A. R., (1983) In Progress in Nucleic Acid Research and Molecular Biology, v. 28, W. E. Cohn, (ed.) 101-142. Academic Press, New York, p. 104. 30S crystals typically reached a maximum size in about 6 weeks at 40C. The largest crystals, which were required for high-resolution data collection, grew to a size of 80±100×80±100×200±300 μm.

Example 2

Computer Based Method of Rational Drug Design

This example provides a computer-based method of rational drug design. To obtain structural information about the protein/drug interaction to allow rational drug design, it is first necessary to prepare a crystal of the complex, the complex being the drug bound to the 30S ribosomal subunit. A crystal of the complex can be produced using two different methods. In a first method, the actual complex itself is crystallized using the prescribed conditions set forth for the native 30S ribosomal subunit. Once crystals of a suitable size have grown, X-ray diffraction data are collected and analyzed as described by Greer et al., *J. of Medicinal Chemistry*, Vol. 37, (1994), 1035-1054. This process usually involves the measurement of many tens of thousands of diffracted X-rays over a period of one to several days depending on the crystal form and the resolution of the data required. According to the method, crystals are bombarded with X-rays. The crystals diffract the rays, creating a geometrically precise splatter of spots on photographic film or electronic detectors. The distribution of atoms within the crystal influences the pattern of spots. Subtraction of the data, $F_{ligand}-F_{native}$, using phases from the atomic model of the 30S ribosomal subunit structure produces the electron density of only the drug molecule. Visualization of the observed electron density superimposed on the atomic coordinates derived from the same crystal form provides a determination of key protein drug interactions that are necessary for rational drug design. In the normal practice of the invention, this would be an iterative process involving several cycles of modeling with each of the new drugs synthesized as a result of the changes suggested by the crystal structure of the complex. In the second commonly practiced method, the drugs or ligands may be soaked into the crystal because of the inherently large aqueous solvent channels present in protein crystals. (See, e.g., Carter et. al., 244 Science, 1195-1198 (1989.) The crystalline complex thus formed follows the same procedure described above to provide the electron density of the drug of interest. Recent advances in rational drug design are described in Gane, P. J. and Dean, P. M. Curr. Op. Struct. Biol. (2000) 10:4:401-404.

Example 3

An Example of a Computer Based Method for Identifying a Potential Inhibitor of the 30S Ribosome This example discloses a computer based method to identify a potential inhibitor of the 30S ribosome. The structure of an antibiotic bound to the 30S defines "crystallographically known sites." A number of molecular docking procedures can be used to design novel binders that also bind to these sites. For example, the programs MCSS and Ludi can be used to dock small fragments that can then be linked together to form a novel ligand. Molecular docking procedures, as used herein, refer to the use of computer programs, as defined herein, to identify potential ligands that are predicted to stably interact with a defined site on the 30S ribosome subunit. Alternatively, libraries of compounds as described herein are converted into 3D format using programs such as Concord (Tripos), CeriusII (Accelrys) etc. The 3D structures of the ligands are then docked against a site on the ribosome. This site can be a confirmed site (i.e. one where there is crystallographic or other evidence of binding of a known molecule) or a novel site. Docking methods typically involve using computer programs DOCK (UCSF), FleXX(Tripos), Ludi(Accelrys), Gold(CCDC, Cambridge, UK). The docking of a compound library results in a "ranking" of the molecules. An energy threshold based on their predicted interaction energy or score. It is possible to choose a "minimum score" and select compounds that are predicted to score better than this minimum value (threshold). This energy threshold is then used to select virtual hits. For example, any ligand that scores better than an arbitrary value −20 would be selected as a hit. Another example would be to select the best scoring 1000 compounds as hits. The selected hits can then be acquired through the companies that supply the compounds (and the catalogues). These compounds are then screened experimentally to identify the "real" hits, i.e. the molecules that are active, as defined herein.

This approach can be extended to those sites where only indirect evidence of functional importance is available, such as results of foot-printing of known antibiotics, 30S mutational data etc. Indeed the 30S structure in the presence or absence of bound antibiotic can be used for the de-novo search of novel binders using docking methods described above.

Example 4 how to Determine the Structure of 30S from a Species that is not *thermophilus*

This example describes how 'molecular replacement' of the known three dimensional structure of the 30S ribosomal subunit of *Thermus thermophilis* can be used to facilitate the structure determination of other 30S ribosomal subunits from non *T. thermophilus* prokaryotes, as defined herein, in particular those that are pathogenic to humans. Molecular replacement, as the name suggests, uses a molecule having a known structure, in this case, the 30S ribosomal subunit of *T. thermophilus*, as a starting point to model the structure of the unknown crystalline sample. This technique is based on the principle that two molecules that have similar structures and similar orientations and positions in the unit cell diffract similarly. Effective use of this technique requires that the structures of the known and unknown molecules be highly homologous. Computer programs used in molecular replacement analyses are AMORE (part of the CCP4 suite; J. Navaza, Acta Cryst. A50, 157-163 (1994)), CNS(X) (Brunger, A. T., Adams, P. D., Clore, G. M., DeLano, W. L., Gros, P., Grosse-Kunstleve, R. W., Jiang, J.-S., Kuszewski, J., Nilges, N., Pannu, N. S., Read, R. J., Rice, L. M., Simonson, T., and Warren, G. L. (1998), Crystallography and NMR system (CNS): A new software system for macromolecular structure determination, Acta Cryst. D54, 905-921); EPMR (Charles R. Kissinger, Daniel K. Gehlhaar & David B. Fogel, "Rapid Automated Molecular Replacement by Evolutionary Search", Acta Crystallographica, Section D, 1999 February; 55 (Pt 2): 484-91; REPLACE (L. Tong J. Appl. Cryst. 26, 748-751, (1993); L. Tong & M. G. Rossmann Acta Cryst. A46, 783-792, (1990)); and MOLREP (A. Vagin, A. Teplyakov, MOLREP: an automated program for molecular replacement., J. Appl. Cryst. (1997) 30, 1022-1025).

In brief, 'molecular replacement' involves positioning the known structure in the unit cell in the same location and orientation as the unknown structure. Once positioned, the atoms of the known structure in the unit cell are used in the so-called Structure Factor Equation to calculate the structure factors that would result from a hypothetical diffraction experiment. The Structure Factor Equation takes the form:

$$F_H = \sum_{j=1}^{N} f_j \exp 2\pi i (hx_j + ky_j + lz_j).$$

where F(H) is the structure factor of the molecule at the point (H=hkl) on the detector surface, $f_j$ is the atomic structure factor (that is, it represents the scattering properties of the individual atom), N is the number of non-hydrogen atoms, and $x_j, y_j, z_j$ are the fractional coordinates of atom j in the unit cell. The structure factor calculated is generally a complex number containing both the amplitude and phase data for the molecular replacement model at each point (hkl) on the detector surface. These phases can then be refined using CNS or other refinement programs to produce even better phases. Finally, the new structure can be built into the density from these phases and the measured amplitudes and then refined to get an accurate structure of the new molecule. These calculated phases are used, in turn, with the experimental amplitudes measured for the unknown structure to calculate an approximate electron distribution. "Refinement" refers to the repeated use of programs such as CNS and involves the computation of rigid body, conjugate gradient minimisation, simulated annealing and conjugate gradient minimisation. The calculated electron density is then inspected and the model is altered by hand or computationally, followed by further rounds of refinement. In this manner, the approximate structure can be fine-tuned to yield a more accurate and often higher resolution structure.

The molecular replacement technique requires knowledge of the number of molecules, and the orientation and position of each molecule within the unit cell as defined herein. Initially, the electron density calculated from the phases from the molecular replacement model and experimental amplitudes closely resembles the electron density of the model. Only after refinement of the initial structure, as described herein, will the success or failure of the method be apparent. For instance, failure occurs if the initial structure fails to converge (as represented by a correlation value) or if the refined structure diverges from the structure of the model during the refinement process. In cases where the unknown structure is a ligand bound to a 30S ribosomal subunit, molecular replacement's success is evident when the result is a structure whose only difference is added electron density that represents the ligand-bound 30S subunit. The determination of such structures is important in the area of pharmaceutical drug testing where the structure of 30S subunit-bound drugs and intermediates yield important information about binding and mechanism. Similarly, new mutants of the 30S subunit or variations of 30S subunit bound inhibitors are well suited for molecular replacement, as are structures of the same molecule that have crystallized in different symmetry groups.

Example 5 a Method of Modelling a Structure of the 30S Ribosomal Subunit Bound to a Modulator This example describes how to model a structure of the 30S ribosomal subunit bound to a modulator. Potential modulators of 30S ribosomal function are examined by computer modeling using docking programs such as GRAM, DOCK, or AUTODOCK [Dunbrack et al., Folding & Design, 2:27-42 (1997)] and the known three dimensional structure of the 30S ribosomal subunit. This procedure can include computer fitting of these potential modulators to ascertain how well the shape and the chemical structure of the potential modulator will bind to the 30S subunit. Computer programs are also employed to estimate the attraction, repulsion, and steric hindrance of the 30S subunit with a modulator/inhibitor.

Example 6

Methods of Designing a Molecule that Interacts with the 30S Ribosomal Subunit

This example describes methods for designing potential drugs that bind specifically to the 30S ribosomal subunit. From the analysis of the structure of the 30S ribosomal subunit in complex with antibiotics, a person skilled in the art will identify the key interactions between the known antibiotic and the 30 S subunit. The spatial arrangements of these interactions identify potential features that a molecule may possess to interact with the 30S. Examples of these features are: hydrogen bond donor, HB acceptor, hydrophobic, aromatic, positively ionisable, negatively ionisable, positive charge, negative charge etc. . . . The relative spatial arrangement of these features (i.e. distances separating each pair of features, angles etc.) defines a set of pharmacophores. Pharmacophores can also be used for the de-novo design of molecules that fulfill the features of the pharmacophore. Computer programs, such as Catalyst (Accelrys) and Unity (Tripos) that generate the parameters defining a pharmacophore, can be used to search large databases of compounds for potential binding partners of the 30S ribosomal subunit. Commonly used databases include the Available Chemical Directory (ACD) from MDL as well as various electronic catalogues of publicly available compounds such as the National Cancer Institute (NCI, US) catalogue, ComGenex catalogue (Budapest, Hungary), Asinex (Moscow, Russia) etc.

For example, the analysis of the interaction between tetracycline and the 30S ribosome shows that only one edge of the tetracycline molecule interacts with the RNA. Furthermore, that edge is composed of a hydoxyl-carbonyl-hydroxyl that potentially interacts with a $Mg^{2+}$ ion present in the binding site. Compound databases are searched for any molecule that displays aligned hydrogen bond donor—hydrogen bond acceptor—hydrogen bond donor, or preferentially hydroxyl-carbonyl-hydroxyl (angle 180+/−10 deg), separated by 2.6 A+/−0.5 A (the pharmacophore). All molecules that fulfill these criteria are identified as potential binders that could be tested in a binding partner assays described herein.

Analysis of the structure of the antibiotics in complex with the 30S ribosomal subunit also enables those skilled in the art to design novel binders by combining 2 or more fragments of interacting molecules. For example, novel molecules may be designed by combining all or parts of paromomycin and streptomycin.

The activity of all molecules designed above can be tested using the described assays.

Example 7

Determination of the Activity of a Binding Partner of the 30S

This example describes functional assays used to determine the activity of a potential binding partner of the 30S ribosomal subunit. Typically these assays include either cell free translation assays or analysis of the 'partial reactions' such as tRNA or mRNA binding that are required for polypeptide chain synthesis.

A. In Vitro Translation.

The ribosome is a molecular machine that makes proteins. A 30S binding partner, useful according to the invention, can inhibit translation. To identify the functional activity of a 30S binding partner, a translational assay can be used as described in Zubay G In vitro synthesis of protein in microbial systems. Annu Rev Genet 1973;7:267-87 in the presence or absence of a putative 30S ribosomal subunit binding partner. A molecule that increases or decreases translation by at least 10% is identified as a binding partner.

B. Partial Reactions.

During protein synthesis, the 30S ribosomal subunit interacts with a large number of ligands—mRNAs, tRNAs, proteins etc. Partial reactions involved in protein synthesis are, therefore, used to demonstrate the inhibition or activation of ribosomal function by a 30S bound compound. There are three main stages of translation—initiation, elongation and termination. Such assays as tRNA binding (as described in Ashraf, S. S., Ansari, G., Guenther, R., Sochacka, E., Malkiewicz, A., Agris, P. F. (1999): The Uridine in "U-turn": Contributions to tRNA-ribosomal Binding. RNA 5, 503-511), and mRNA binding (as described in Von Ahsen, U., Green, R., Schroeder, R., Noller, H. (1997): Identification of 2'hydroxyl Groups Required for Interaction of a tRNA Anticodon Stem-loop Region with the Ribosome. RNA 3:49-56) are performed in the presence or absence of a putative 30S modulator to identify inhibitors or activators that which modulate the function of 30S subunit.tRNA binding and/or mRNA binding.

Example 8

A Method of Preparing a Computer Fitting Model of Binding of a Binding Partner of the 30S Subunit and the 30S Subunit Starting with the 3D coordinates of the 30S ribosomal subunit structure, a co-factor or binding partner, such as tRNA, mRNA, or EF-G protein, is manually docked into its binding site based upon biochemical data and making use of standard molecular graphics software packages (such as QUANTA or INSIGHT from Accelrys). The in silico coordinates of the complex thus generated is then refined using energy minimisation algorithms as described elsewhere (under modelling of mutated ribosome). An example of a similar procedure is the modelling of the 70S ribosome structure complexed with ribosomal protein S8 based on high resolution coordinates of the 30S and 50S ribosome structures (Lancaster L, Culver G M, Yusupova G Z, Cate J H, Yusupov M M, Noller H F., (2000) RNA May; 6(5): 717-729.

Example 9 a Method of Characterizing Binding of a Binding Partner of the 30S Subunit to the 30S Subunit This example describes commonly used methods to characterize potential binding partners of the 30S ribosomal subunit.

A. Binding of Radioactively Labelled Compounds to the 30S Ribosomal Subunit.

This approach was successfully used for the identification of some ribosomal binders, for example, $^3$H-labelled tetracycline, chloramphenicol, oxazolidinones etc. Direct binding of the radioactive compound or the displacement of the known radioactive 30S binding partner (known antibiotics) by different compounds can be used for identification of the potential 30S binder as described in Matassova N. B., Rodnina M. V., Endennann R., Kroll H. P., Pleiss U., Wild H., Wintermeyer W. Ribosomal RNA is the target for oxazolidinones, a novel class of translational inhibitors. RNA. 1999. V. 5. P.

939-946; Bischof O, Urlaub H, Kruft V, Wittmann-Liebold B Peptide environment of the peptidyl transferase center from *Eschenchia coli* 70 S ribosomes as determined by thermoaffinity labeling with dihydrospiramycin. J Biol Chem 1995 Sep. 29; 270(39): 23060-4 and Bischof O, Kruft V, Wittmann-Liebold B Analysis of the puromycin binding site in the 70 S ribosome of *Escherichia coli* at the peptide level. J Biol Chem 1994 Jul. 15; 269(28): 18315-9.

B. Fluorescence Techniques—the Binding and Displacement of Fluorescently Labelled Antibiotics to 30S Ribosomal Subunits.

The binding or displacement of fluorescently labelled antibiotics or RNA binding ligands to 30S ribosomal subunits can be measured by a number of fluorescence techniques, including fluorescence anisotropy or polarisation, the enhancement of fluorescence on binding and the quenching of fluorescence on binding.

Polarisation P $$P = (I_\| - I\perp)/(I_\| + I\perp)$$

The anisotropy r $$r = ((I_\| I\perp)/(I_\| + 2I\perp)$$

$I_\|$ is the intensity of the emission viewed through parallel polarisers and $I\perp$ is the intensity of the emission viewed through perpendicularly arranged polarisers. In solution fluorescent molecules are generally rotationally free and measured anisotropies are low. On binding, they become rotationally constrained and their anisotropy increases to a maximum value as described in Epe B, Woolley P, Hornig Competition between tetracycline and tRNA at both P and A sites of the ribosome of *Escherichia coli*. FEBS Lett 1987 Mar. 23;213(2):443-7 and Epe B, Woolley P. The binding of 6-demethylchlortetracycline to 70S, 50S and 30S ribosomal particles: a quantitative study by fluorescence anisotropy. EMBO J. 1984 Jan.; 3(1):121-6.

Anisotropy can therefore be used to measure binding of a fluorescently labelled antibiotic or RNA binding ligand to a 30S ribosomal subunit. Fluorescence polarisation can be also used to measure binding of a fluorescently labelled antibiotic or RNA binding ligand to a large RNA molecule or ribonucleoprotein complex.

Example 10

A Method of Analyzing a 30S Ligand Complex

The 30S ligand complex is analysed as described in Barrett J F (2000) Linezolid Pharmacia Corp Curr Opin Investig Drugs 1(2): 181-7; Lin A H, Murray R W, Vidmar T J, Marotti K R (1997) Antimicrob Agents Chemother 41(10): 2127-31; Epe B, Woolley P, Hornig (1987) FEBS Lett 213(2): 443-7 and Epe B, Woolley P. (1984) EMBO J. 3(1):121-6.

Example 11

A Method of Modelling the Structure of a Mutant 30S Subunit

The structure of the ribosome is visualised using a standard molecular modelling package such as Insight (Accelrys). Using the graphical tools, it is possible to interact with the 3D coordinates of selected RNA bases or protein side chains and mutate them. The 3D coordinates are then refined using standard molecular mechanics tools for energy minimisation (such as CHARMM, Insight (Accelrys)). The refined coordinates are then saved in electronic format and used for subsequent drug design work.

Although the foregoing invention has been described in some detail by way of illustration and example for purposes of clarity of understanding, it will be apparent to those skilled in the art that certain changes and modifications may be practised. Therefore, the descriptions and examples should not be construed as limiting the scope of the invention, which is delineated by the appended claims.

REFERENCES

1. Garrett, R. A. et al. (eds.) The Ribosome. Structure, Function, Antibiotics and Cellular Interactions (ASM Press, Washington, D.C., 2000).
2. von Böhlen, K. et al. Characterization and preliminary attempts for derivatization of crystals of large ribosomal subunits from Haloarcula marismortui diffracting to 3 Å resolution. J. Mol. Biol. 222, 11-15 (1991).
3. Trakhanov, S. D. et al. Crystallization of 70 S ribosomes and 30 S ribosomal subunits from *Thermus thermophilus*. FEBS Lett. 220, 319-322 (1987).
4. Glotz, C. et al. Three-dimensional crystals of ribosomes and their subunits from eu- and archaebacteria. Biochem. Int. 15, 953-960 (1987).
5. Yonath, A. et al. Characterization of crystals of small ribosomal subunits. J. Mol. Biol. 203, 831-834 (1988).
6. Yusupov, M. M., Tischenko, S. V., Trakhanov, S. D., Ryazantsev, S. N. & Garber, M. B. A new crystalline form of 30 S ribosomal subunits from *Thermus thermophilus*. FEBS Lett. 238, 113-115 (1988).
7. Yonath, A. et al. Crystallographic studies on the ribosome, a large macromolecular assembly exhibiting severe nonisomorphism, extreme beam sensitivity and no internal symmetry. Acta Crystallogr A54, 945-55 (1998).
8. Tocilj, A. et al. The small ribosomal subunit from *Thermus thermophilus* at 4.5 A resolution: pattern fittings and the identification of a functional site. Proc Natl Acad Sci USA 96, 14252-7 (1999).
9. Clemons, W. M., Jr. et al. Structure of a bacterial 30S ribosomal subunit at 5.5 Å resolution. Nature 400, 833-840 (1999).
10. Otwinowski, Z. & Minor, W. in Methods in Enzymology (eds. Carter, C. W. J. & Sweet, R. M.) 307-25 (Academic Press, New York, 1997).
11. Terwilliger, T. & Berendzen, J. Automated MAD and MIR structure determination. Acta Cryst D55, 849-861 (1999).
12. Abrahams, J. P. Bias reduction in phase refinement by modified interference functions: introducing the gamma correction. Acta Cryst. D53 (1997).
13. de la Fortelle, E. & Bricogne, G. in Methods in Enzymology (eds. Carter, C. W., Jr. & Sweet, R. M.) 472-93 (Academic Press, New York, 1997).
14. Hartmann, R. K. & Erdmann, V. A. *Thermus* thermophilus 16S rRNA is transcribed from an isolated transcription unit. J Bacteriol 171, 2933-41 (1989).
15. Cowtan, K. & Main, P. Miscellaneous algorithms for density modification. Acta Crystallogr D Biol Crystallogr 54, 487-93 (1998).
16. Jones, T. A. & Kjeldgaard, M. Electron-density map interpretation. Meth. Enzymol. 277B, 173-207 (1997).
17. Brünger, A. T. et al. Crystallography & NMR system: A new software suite for macromolecular structure determination. Acta Crystallogr D Biol Crystallogr 54, 905-21 (1998).
18. Choli, T., Franceschi, F., Yonath, A. & Wittmann-Liebold, B. Isolation and characterization of a new ribosomal protein from the thermophilic eubacteria, *Thermus thermophilus, T. aquaticus* and *T. flavus*. Biol Chem Hoppe Seyler 374, 377-83 (1993).
19. Mueller, F. & Brimacombe, R. A new model for the three-dimensional folding of *Escherichia coli* 16 S ribosomal RNA. I. Fitting the RNA to a 3D electron microscopic map at 20 A. J Mol Biol 271, 524-44 (1997).
20. Mougel, M. et al. Minimal 16S rRNA binding site and role of conserved nucleotides in *Escherichia coli* ribosomal protein S8 recognition. Eur J Biochem 215, 787-92 (1993).
21. Wu, H., Jiang, L. & Zimmermann, R. A. The binding site for ribosomal protein S8 in 16S rRNA and spc mRNA from *Escherichia coli*: minimum structural requirements and the effects of single bulged bases on S8-RNA interaction. Nucleic Acids Res 22, 1687-95 (1994).
22. Urlaub, H., Thiede, B., Muller, E. C., Brimacombe, R. & Wittmann-Liebold, B. Identification and sequence analysis of contact sites between ribosomal proteins and rRNA in *Escherichia coli* 30 S subunits by a new approach using matrix-assisted laser desorption/ionization-mass spectrometry combined with N-terminal microsequencing. J Biol Chem 272, 14547-55 (1997).
23. Golden, B. L., Hoffman, D. W., Ramakrishnan, V. & White, S. W. Ribosomal protein S17: characterization of the three-dimensional structure by 1H- and 15N-NMR. Biochemistry 32, 12812-20 (1993).
24. Allard, P. et al. Another piece of the ribosome: Solution structure of S16 and its location in the 30S subunit. Structure, (2000).
25. Davies, C., Gerstner, R. B., Draper, D. E., Ramakrishnan, V. & White, S. W. The crystal structure of ribosomal protein S4 reveals a two-domain molecule with an extensive RNA-binding surface: one domain shows structural homology to the ETS DNA-binding motif. EMBO J. 17, 4545-58 (1998).
26. Markus, M. A., Gerstner, R. B., Draper, D. E. & Torchia, D. A. The solution structure of ribosomal protein S4 delta41 reveals two subdomains and a positively charged surface that may interact with RNA. Embo J 17, 4559-71 (1998).
27. van Acken, U. Protein chemical studies on ribosomal proteins S4 and S12 from ram (ribosomal ambiguity) mutants of *Escherichia coli*. Mol Gen Genet 140, 61-8 (1975).
28. Wittmann-Liebold, B. & Greuer, B. The primary structure of protein S5 from the small subunit of the *Escherichia coli* ribosome. FEBS Lett 95, 91-8 (1978).
29. Nowotny, V. & Nierhaus, K. H. Assembly of the 30S subunit from *Escherichia coli* ribosomes occurs via two assembly domains which are initiated by S4 and S7. Biochemistry 27, 7051-5 (1988).
30. Tanaka, I. et al. Matching the crystallographic structure of ribosomal protein S7 to a three-dimensional model of the 16S ribosomal RNA. Rna 4, 542-50 (1998).
31. Helgstrand, M. et al. Solution structure of the ribosomal protein S19 from *Thermus thermophilus*. J Mol Biol 292, 1071-81 (1999).
32. Lodmell, J. S. & Dahlberg, A. E. A conformational switch in *Escherichia coli* 16S ribosomal RNA during decoding of messenger RNA. Science 277, 1262-7 (1997).
33. Rose, S. J. d., Lowary, P. T. & Uhlenbeck, O. C. Binding of yeast tRNAPhe anticodon arm to *Escherichia coli* 30 S ribosomes. J Mol Biol 167, 103-17 (1983).
34. Huttenhofer, A. & Noller, H. F. Hydroxyl radical cleavage of tRNA in the ribosomal P-site. Proc Natl Acad Sci USA 89, 7851-5 (1992).
35. Jack, A., Ladner, J. E. & Klug, A. Crystallographic refinement of yeast phenylalanine transfer RNA at 2-5 A resolution. J Mol Biol 108, 619-49 (1976).
36. Rich, A. & RajBhandary, U. L. Transfer RNA: molecular structure, sequence, and properties. Annu Rev Biochem 45, 805-60 (1976).
37. Moazed, D. & Noller, H. F. Binding of tRNA to the ribosomal A and P-sites protects two distinct sets of nucleotides in 16 S rRNA. J Mol Biol 211, 135-45 (1990).
38. Prince, J. B., Taylor, B. H., Thurlow, D. L., Ofengand, J. & Zimmermann, R. A. Covalent crosslinking of tRNA1Val to 16S RNA at the ribosomal P-site: identification of crosslinked residues. Proc Natl Acad Sci USA 79, 5450-4 (1982).
39. Cate, J. H., Yusupov, M. M., Yusupova, G. Z., Earnest, T. N. & Noller, H. F. X-ray crystal structures of 70S ribosome functional complexes see comments]. Science 285, 2095-104 (1999).
40. von Ahsen, U. & Noller, H. F. Identification of bases in 16S rRNA essential for tRNA binding at the 30S ribosomal P-site. Science 267, 234-7 (1995).
41. Gabashvili, 1. S. et al. Major rearrangements in the 70S ribosomal 3D structure caused by a conformational switch in 16S ribosomal RNA. *EMBO J.* 18, 6501-7 (1999).

TABLE 2

REMARK 465 MISSING RESIDUES
REMARK 465 THE FOLLOWING RESIDUES WERE NOT LOCATED
IN THE REMARK 465 EXPERIMENT.
(M = MODEL NUMBER; RES = RESIDUE NAME;
C = CHAIN REMARK 465 IDENTIFIER;
SSSEQ = SEQUENCE NUMBER; I = INSERTION CODE.)

| | M | RES | C | SSSEQI |
|---|---|---|---|---|
| REMARK 465 | | | | |
| REMARK 465 | U | | A | 0 |
| REMARK 465 | U | | A | 1 |
| REMARK 465 | U | | A | 2 |
| REMARK 465 | G | | A | 3 |
| REMARK 465 | U | | A | 4 |
| REMARK 465 | C | | A | 1535 |
| REMARK 465 | C | | A | 1536 |
| REMARK 465 | U | | A | 1537 |
| REMARK 465 | C | | A | 1538 |
| REMARK 465 | C | | A | 1539 |
| REMARK 465 | U | | A | 1540 |
| REMARK 465 | U | | A | 1541 |
| REMARK 465 | U | | A | 1542 |
| REMARK 465 | C | | A | 1543 |
| REMARK 465 | U | | A | 1544 |
| REMARK 465 | MET | | B | 1 |
| REMARK 465 | PRO | | B | 2 |
| REMARK 465 | VAL | | B | 3 |
| REMARK 465 | GLU | | B | 4 |
| REMARK 465 | ILE | | B | 5 |
| REMARK 465 | THR | | B | 6 |
| REMARK 465 | GLU | | B | 241 |
| REMARK 465 | ALA | | B | 242 |
| REMARK 465 | GLU | | B | 243 |
| REMARK 465 | ALA | | B | 244 |
| REMARK 465 | THR | | B | 245 |
| REMARK 465 | GLU | | B | 246 |
| REMARK 465 | THR | | B | 247 |
| REMARK 465 | PRO | | B | 248 |
| REMARK 465 | GLU | | B | 249 |
| REMARK 465 | GLY | | B | 250 |
| REMARK 465 | GLU | | B | 251 |
| REMARK 465 | SER | | B | 252 |
| REMARK 465 | GLU | | B | 253 |
| REMARK 465 | VAL | | B | 254 |
| REMARK 465 | GLU | | B | 255 |
| REMARK 465 | ALA | | B | 256 |
| REMARK 465 | MET | | C | 1 |
| REMARK 465 | ILE | | C | 208 |
| REMARK 465 | GLY | | C | 209 |

TABLE 2-continued

REMARK 465 MISSING RESIDUES
REMARK 465 THE FOLLOWING RESIDUES WERE NOT LOCATED
IN THE REMARK 465 EXPERIMENT.
(M = MODEL NUMBER; RES = RESIDUE NAME;
C = CHAIN REMARK 465 IDENTIFIER;
SSSEQ = SEQUENCE NUMBER; I = INSERTION CODE.)

| | | | |
|---|---|---|---|
| REMARK 465 | GLY | C | 210 |
| REMARK 465 | GLN | C | 211 |
| REMARK 465 | LYS | C | 212 |
| REMARK 465 | PRO | C | 213 |
| REMARK 465 | LYS | C | 214 |
| REMARK 465 | ALA | C | 215 |
| REMARK 465 | ARG | C | 216 |
| REMARK 465 | PRO | C | 217 |
| REMARK 465 | GLU | C | 218 |
| REMARK 465 | LEU | C | 219 |
| REMARK 465 | PRO | C | 220 |
| REMARK 465 | LYS | C | 221 |
| REMARK 465 | ALA | C | 222 |
| REMARK 465 | GLU | C | 223 |
| REMARK 465 | GLU | C | 224 |
| REMARK 465 | ARG | C | 225 |
| REMARK 465 | PRO | C | 226 |
| REMARK 465 | ARG | C | 227 |
| REMARK 465 | ARG | C | 228 |
| REMARK 465 | ARG | C | 229 |
| REMARK 465 | ARG | C | 230 |
| REMARK 465 | PRO | C | 231 |
| REMARK 465 | ALA | C | 232 |
| REMARK 465 | VAL | C | 233 |
| REMARK 465 | ARG | C | 234 |
| REMARK 465 | VAL | C | 235 |
| REMARK 465 | LYS | C | 236 |
| REMARK 465 | LYS | C | 237 |
| REMARK 465 | GLU | C | 238 |
| REMARK 465 | GLU | C | 239 |
| REMARK 465 | MET | D | 1 |
| REMARK 465 | MET | E | 1 |
| REMARK 465 | PRO | E | 2 |
| REMARK 465 | GLU | E | 3 |
| REMARK 465 | THR | E | 4 |
| REMARK 465 | GLU | E | 155 |
| REMARK 465 | ALA | E | 156 |
| REMARK 465 | HIS | E | 157 |
| REMARK 465 | ALA | E | 158 |
| REMARK 465 | GLN | E | 159 |
| REMARK 465 | ALA | E | 160 |
| REMARK 465 | GLN | E | 161 |
| REMARK 465 | GLY | E | 162 |
| REMARK 465 | MET | G | 1 |
| REMARK 465 | MET | I | 1 |
| REMARK 465 | MET | J | 1 |
| REMARK 465 | PRO | J | 2 |
| REMARK 465 | VAL | J | 101 |
| REMARK 465 | GLY | J | 102 |
| REMARK 465 | GLY | J | 103 |
| REMARK 465 | GLY | J | 104 |
| REMARK 465 | ARG | J | 105 |
| REMARK 465 | MET | K | 1 |
| REMARK 465 | ALA | K | 2 |
| REMARK 465 | LYS | K | 3 |
| REMARK 465 | LYS | K | 4 |
| REMARK 465 | PRO | K | 5 |
| REMARK 465 | SER | K | 6 |
| REMARK 465 | LYS | K | 7 |
| REMARK 465 | LYS | K | 8 |
| REMARK 465 | LYS | K | 9 |
| REMARK 465 | VAL | K | 10 |
| REMARK 465 | MET | L | 1 |
| REMARK 465 | VAL | L | 2 |
| REMARK 465 | ALA | L | 3 |
| REMARK 465 | LEU | L | 4 |
| REMARK 465 | ALA | L | 129 |
| REMARK 465 | LYS | L | 130 |
| REMARK 465 | THR | L | 131 |
| REMARK 465 | ALA | L | 132 |
| REMARK 465 | ALA | L | 133 |
| REMARK 465 | LYS | L | 134 |
| REMARK 465 | LYS | L | 135 |

TABLE 2-continued

REMARK 465 MISSING RESIDUES
REMARK 465 THE FOLLOWING RESIDUES WERE NOT LOCATED
IN THE REMARK 465 EXPERIMENT.
(M = MODEL NUMBER; RES = RESIDUE NAME;
C = CHAIN REMARK 465 IDENTIFIER;
SSSEQ = SEQUENCE NUMBER; I = INSERTION CODE.)

| | | | |
|---|---|---|---|
| REMARK 465 | MET | M | 1 |
| REMARK 465 | MET | N | 1 |
| REMARK 465 | MET | O | 1 |
| REMARK 465 | ALA | P | 84 |
| REMARK 465 | ARG | P | 85 |
| REMARK 465 | GLU | P | 86 |
| REMARK 465 | GLY | P | 87 |
| REMARK 465 | ALA | P | 88 |
| REMARK 465 | MET | Q | 1 |
| REMARK 465 | MET | R | 1 |
| REMARK 465 | SER | R | 2 |
| REMARK 465 | THR | R | 3 |
| REMARK 465 | LYS | R | 4 |
| REMARK 465 | ASN | R | 5 |
| REMARK 465 | ALA | R | 6 |
| REMARK 465 | LYS | R | 7 |
| REMARK 465 | PRO | R | 8 |
| REMARK 465 | LYS | R | 9 |
| REMARK 465 | LYS | R | 10 |
| REMARK 465 | GLU | R | 11 |
| REMARK 465 | ALA | R | 12 |
| REMARK 465 | GLN | R | 13 |
| REMARK 465 | ARG | R | 14 |
| REMARK 465 | ARG | R | 15 |
| REMARK 465 | MET | S | 1 |
| REMARK 465 | GLY | S | 82 |
| REMARK 465 | HIS | S | 83 |
| REMARK 465 | GLY | S | 84 |
| REMARK 465 | LYS | S | 85 |
| REMARK 465 | GLU | S | 86 |
| REMARK 465 | ALA | S | 87 |
| REMARK 465 | LYS | S | 88 |
| REMARK 465 | ALA | S | 89 |
| REMARK 465 | THR | S | 90 |
| REMARK 465 | LYS | S | 91 |
| REMARK 465 | LYS | S | 92 |
| REMARK 465 | LYS | S | 93 |
| REMARK 465 | MET | T | 1 |
| REMARK 465 | ALA | T | 2 |
| REMARK 465 | GLN | T | 3 |
| REMARK 465 | LYS | T | 4 |
| REMARK 465 | LYS | T | 5 |
| REMARK 465 | PRO | T | 6 |
| REMARK 465 | LYS | T | 7 |
| REMARK 465 | LYS | V | 26 |
| REMARK 465 | LYS | V | 27 |

The invention claimed is:

1. A method of identifying an inhibitor of a 30S ribosomal subunit comprising the steps of:
   (a) characterizing an active site of said 30S ribosomal subunit from *Thermus thermophilus* defined by x-ray atomic coordinate data of Table 1A or Table 1B or an active site of the 30S ribosomal subunit derived from said x-ray atomic coordinate data,
   (b) designing or selecting an inhibitor that interacts with said active site, and
   (c) synthesizing the inhibitor of step (b).

2. The method of claim 1, wherein said active site is characterized from the three-dimensional structure of the 30S subunit.

3. The method of claim 1, wherein said active site is characterized from the three-dimensional structure of at least one sub-domain of the 30S subunit.

4. The method of claim 1 wherein the active site of step (a) is characterized by molecular replacement using the x-ray atomic coordinate data.

* * * * *

UNITED STATES PATENT AND TRADEMARK OFFICE
CERTIFICATE OF CORRECTION

PATENT NO. : 7,606,670 B2  Page 1 of 1
APPLICATION NO. : 09/953807
DATED : October 20, 2009
INVENTOR(S) : Ramakrishnan et al.

It is certified that error appears in the above-identified patent and that said Letters Patent is hereby corrected as shown below:

On the title page,

Item [*] Notice: Subject to any disclaimer, the term of this patent is extended or adjusted under 35 USC 154(b) by 337 days Delete the phrase "by 337 days" and insert -- by 797 days --

Signed and Sealed this

Twentieth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,606,670 B2  Page 1 of 1
APPLICATION NO. : 09/953807
DATED : October 20, 2009
INVENTOR(S) : Ramakrishnan et al.

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by 1257 days Delete the phrase "by 797 days" and insert -- by 1257 days --

Signed and Sealed this

Fourteenth Day of September, 2010

David J. Kappos
*Director of the United States Patent and Trademark Office*